(12) United States Patent
Shelton, IV et al.

(10) Patent No.: US 12,310,582 B2
(45) Date of Patent: May 27, 2025

(54) CONTROL CIRCUIT FOR ACTUATING MOTORIZED FUNCTION OF SURGICAL STAPLING INSTRUMENT UTILIZING INERTIAL DRIVE TRAIN PROPERTIES

(71) Applicant: Cilag GmbH International, Zug (CH)

(72) Inventors: Frederick E. Shelton, IV, Hillsboro, OH (US); Shane R. Adams, Lebanon, OH (US); Taylor W. Aronhalt, Loveland, OH (US); Nicholas J. Ross, Franklin, OH (US); Adam D. Hensel, Gahanna, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/379,766

(22) Filed: Oct. 13, 2023

(65) Prior Publication Data
US 2025/0120697 A1    Apr. 17, 2025

(51) Int. Cl.
*A61B 17/072* (2006.01)
*A61B 17/00* (2006.01)

(52) U.S. Cl.
CPC .. *A61B 17/072* (2013.01); *A61B 2017/00022* (2013.01); *A61B 2017/00398* (2013.01)

(58) Field of Classification Search
USPC ...................................... 227/175.1
See application file for complete search history.

(56) References Cited

U.S. PATENT DOCUMENTS

| | | | |
|---|---|---|---|
| 9,072,535 B2 | 7/2015 | Shelton, IV et al. | |
| 2019/0125432 A1* | 5/2019 | Shelton, IV | ....... A61B 17/1285 |
| 2019/0200981 A1 | 7/2019 | Harris et al. | |
| 2020/0054401 A1* | 2/2020 | Yu | .......... B25J 9/1633 |
| 2022/0105639 A1* | 4/2022 | Zhang | .................... B25J 9/1689 |

* cited by examiner

*Primary Examiner* — Chinyere J Rushing-Tucker

(57) ABSTRACT

A surgical stapling system is disclosed. The stapling system comprises a motor, a drive assembly comprising a drive train coupled to the motor to actuate a function of a surgical end effector, wherein the drive train is actuatable by the motor through a drive stroke, and a control circuit coupled to the drive assembly. The control circuit is configured to monitor a first parameter of the drive assembly during the drive stroke, determine a stored kinetic energy of the drive assembly based on the first parameter, monitor a second parameter of the drive assembly during the drive stroke, wherein the first parameter and the second parameter are different, compare the monitored second parameter to a parameter threshold indicative of a motor stall condition, and determine a motor setting of the motor based on the determined stored kinetic energy and the comparison of the monitored second parameter to the parameter threshold.

20 Claims, 8 Drawing Sheets

CONTROL CIRCUIT FOR ACTUATING MOTORIZED FUNCTION OF SURGICAL STAPLING INSTRUMENT UTILIZING INERTIAL DRIVE TRAIN PROPERTIES

BACKGROUND

In accordance with the present disclosure, a surgical instrument is utilized in a surgical operating environment. The surgical instrument may be handheld and/or attached to and controlled by a surgical robot. In accordance with the present disclosure, the surgical instrument may comprise a surgical stapling instrument configure to clamp, staple, and cut patient tissue during a surgical procedure. Additionally, in accordance with the present disclosure, the surgical instrument may comprise a drive train configured to actuate one or more functions of the surgical stapling instrument. In accordance with the present disclosure, one or more functions of the surgical stapling instrument may be motor driven. Further, in accordance with the present disclosure, a motor control circuit can be provided which controls the motor and, thus, the one or more functions of the surgical stapling instruments.

SUMMARY

A surgical stapling system is disclosed. The stapling system comprises a motor, a drive assembly comprising a drive train coupled to the motor to actuate a function of a surgical end effector, wherein the drive train is actuatable by the motor through a drive stroke, and a control circuit coupled to the drive assembly. The control circuit is configured to monitor a first parameter of the drive assembly during the drive stroke, determine a stored kinetic energy of the drive assembly based on the first parameter, monitor a second parameter of the drive assembly during the drive stroke, wherein the first parameter and the second parameter are different, compare the monitored second parameter to a parameter threshold indicative of a motor stall condition, and determine a motor setting of the motor based on the determined stored kinetic energy and the comparison of the monitored second parameter to the parameter threshold.

BRIEF DESCRIPTION OF THE DRAWINGS

In the description, for purposes of explanation and not limitation, specific details are set forth, such as particular aspects, procedures, techniques, etc. to provide a thorough understanding of the present technology. However, it will be apparent to one skilled in the art that the present technology may be practiced in other aspects that depart from these specific details.

The accompanying drawings, where like reference numerals refer to identical or functionally similar elements throughout the separate views, together with the detailed description below, are incorporated in and form part of the specification, and serve to further illustrate aspects of concepts that include the claimed disclosure and explain various principles and advantages of those aspects.

Corresponding reference characters indicate corresponding parts throughout the several views. The exemplifications set out herein illustrate various embodiments of the invention.

DESCRIPTION

Figure 1:
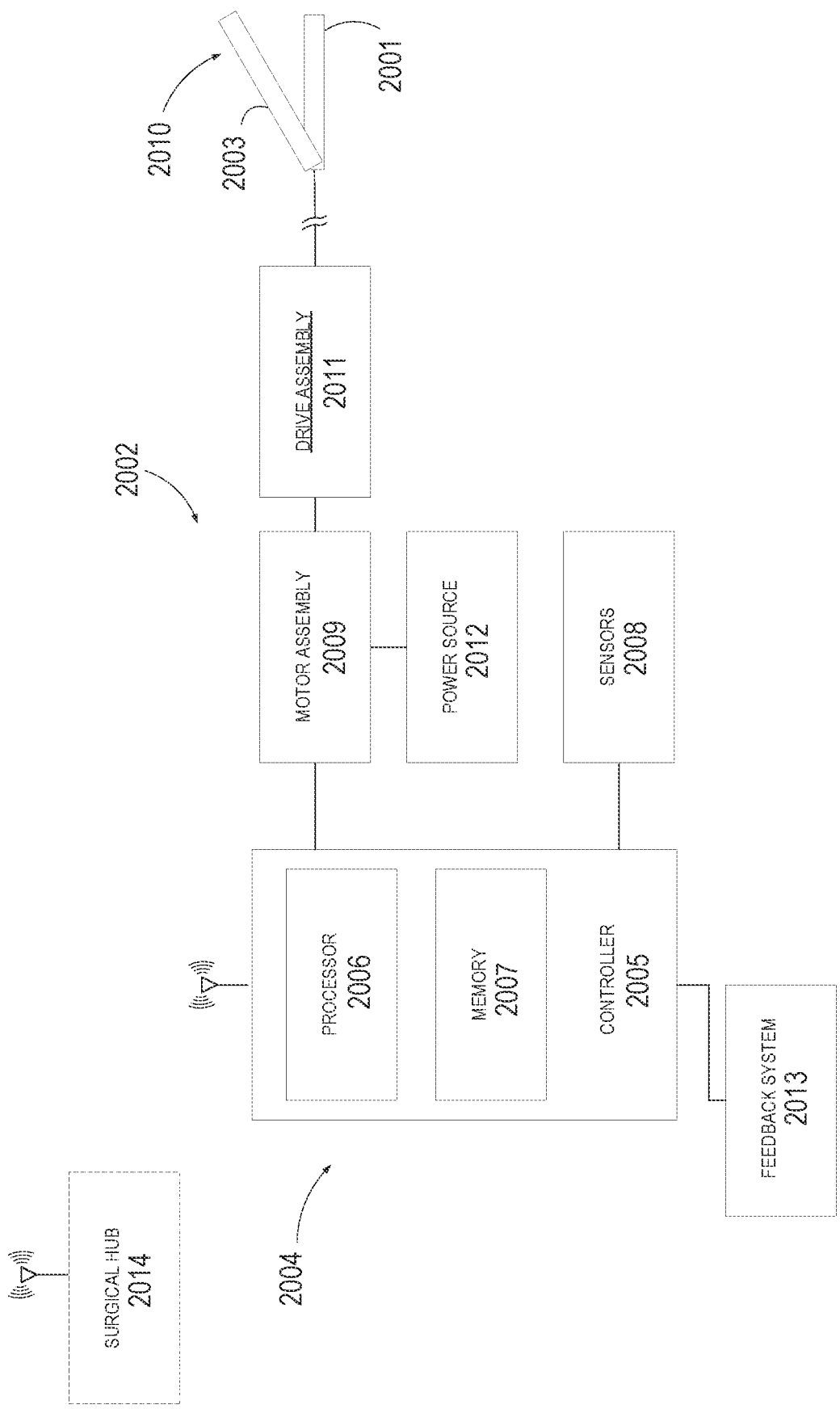
FIG. 1 is a block diagram of a surgical system comprising an end effector, a motor-driven drive assembly, and a control circuit configured to control actuation of the motor-driven drive assembly, in accordance with the present disclosure.

Applicant of the present application owns the following U.S. Patent Applications that were filed on-even date herewith Oct. 13, 2023 and which are each herein incorporated by reference in their respective entireties:

- U.S. patent application Ser. No. 18/379,759, titled METHOD OF OPERATING A SURGICAL STAPLING INSTRUMENT;
- U.S. patent application Ser. No. 18/379,762, titled SURGICAL STAPLING SYSTEMS WITH ADAPTIVE STAPLE FIRING ALGORITHMS;
- U.S. patent application Ser. No. 18/379,763, titled LEARNED TRIGGERS FOR ADAPTIVE CONTROL OF SURGICAL STAPLING SYSTEMS;
- U.S. patent application Ser. No. 18/379,768, titled PROPORTIONATE BALANCING OF THE FUNCTION IMPACT MAGNITUDE OF BATTERY OUTPUT TO PEAK MOTOR CURRENT;
- U.S. patent application Ser. No. 18/379,771, titled MOTOR OPTIMIZATION BY MINIMIZATION OF PARASITIC LOSSES AND TUNING MOTOR DRIVE CONFIGURATION;
- U.S. patent application Ser. No. 18/379,773, titled APPARATUS AND METHOD TO REDUCE PARASITIC LOSSES OF THE ELECTRICAL SYSTEM OF A SURGICAL INSTRUMENT;
- U.S. patent application Ser. No. 18/379,776, titled SURGICAL TOOL WITH RELAXED FLEX CIRCUIT ARTICULATION;
- U.S. patent application Ser. No. 18/379,777, titled WIRING HARNESS FOR SMART STAPLER WITH MULTI AXIS ARTICULATION;
- U.S. patent application Ser. No. 18/379,781, titled SURGICAL SYSTEM WITH WIRELESS ARRAY FOR POWER AND DATA TRANSFER; and
- U.S. patent application Ser. No. 18/379,784, titled SURGICAL STAPLE CARTRIDGE COMPRISING REPLACEABLE ELECTRONICS PACKAGE.

Applicant of the present application owns the following U.S. Patent Applications that were filed on-even date herewith Oct. 13, 2023 and which are each herein incorporated by reference in their respective entireties:

- U.S. patent application Ser. No. 18/379,790, titled METHOD OF ASSEMBLING A STAPLE CARTRIDGE;
- U.S. patent application Ser. No. 18/379,793, titled CONTROL SURFACES ON A STAPLE DRIVER OF A SURGICAL STAPLE CARTRIDGE;
- U.S. patent application Ser. No. 18/379,796, titled INTEGRAL CARTRIDGE STIFFENING FEATURES TO REDUCE CARTRIDGE DEFLECTION;
- U.S. patent application Ser. No. 18/379,801, titled STAPLE CARTRIDGE COMPRISING WALL STRUCTURES TO REDUCE CARTRIDGE DEFLECTION;
- U.S. patent application Ser. No. 18/379,803, titled PANLESS STAPLE CARTRIDGE ASSEMBLY COMPRISING RETENTION FEATURES FOR HOLDING STAPLE DRIVERS AND SLED;
- U.S. patent application Ser. No. 18/379,805, titled STAPLE CARTRIDGE COMPRISING A SLED HAVING A DRIVER LIFT CAM;
- U.S. patent application Ser. No. 18/379,808, titled SURGICAL STAPLE CARTRIDGES WITH SLEDS CONFIGURED TO BE COUPLED TO A FIRING DRIVER OF A COMPATIBLE SURGICAL STAPLER;
- U.S. patent application Ser. No. 18/379,810, titled STAPLE CARTRIDGE COMPRISING A COMPOSITE SLED;
- U.S. patent application Ser. No. 18/379,811, titled SURGICAL INSTRUMENTS WITH JAW AND FIRING ACTUATOR LOCKOUT ARRANGEMENTS LOCATED PROXIMAL TO A JAW PIVOT LOCATION;
- U.S. patent application Ser. No. 18/379,815, titled SURGICAL INSTRUMENTS WITH LATERALLY ENGAGEABLE LOCKING ARRANGEMENTS FOR LOCKING A FIRING ACTUATOR;
- U.S. patent application Ser. No. 18/379,817, titled DUAL INDEPENDENT KEYED LOCKING MEMBERS ACTING ON THE SAME DRIVE MEMBER;
- U.S. patent application Ser. No. 18/379,820, titled ADJUNCTS FOR USE WITH SURGICAL STAPLING INSTRUMENTS;
- U.S. patent application Ser. No. 18/379,822, titled ADJUNCTS FOR USE WITH SURGICAL STAPLING INSTRUMENTS;
- U.S. patent application Ser. No. 18/379,826, titled JAW CONTROL SURFACES ON A SURGICAL INSTRUMENT JAW;
- U.S. patent application Ser. No. 18/379,827, titled ZONED ALGORITHM ADAPTIVE CHANGES BASED ON CORRELATION OF COOPERATIVE COMPRESSION CONTRIBUTIONS OF TISSUE;
- U.S. patent application Ser. No. 18/379,831, titled STAPLE CARTRIDGES COMPRISING TRACE RETENTION FEATURES; and
- U.S. patent application Ser. No. 18/379,832, titled STAPLE CARTRIDGES COMPRISING STAPLE RETENTION FEATURES.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the described and illustrated embodiments are non-limiting examples, and thus it can be appreciated that the specific structural and functional details disclosed herein may be representative and illustrative. Variations and changes may be made without departing from the scope of the claims.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working frame through which the end effector and elongate shaft of a surgical instrument can be advanced.

FIG. 1 illustrates a block diagram of a surgical system 2002 for use with one or more surgical instruments, tools, and/or robotic systems in accordance with one or more aspects of the present disclosure. The system 2002 includes a control circuit 2004. The control circuit 2004 includes a microcontroller 2005 comprising a processor 2006 and a storage medium such as, for example, a memory 2007.

A motor assembly 2009 includes one or more motors, driven by motor drivers. The motor assembly 2009 operably couples to a drive assembly 2011 to drive, or effect, one or more motions at an end effector 2010. The drive assembly 2011 may include any number of components suitable for transmitting motion to the end effector 2010 such as, for example, one or more gears, gear sets, gear transmissions with one or multiple selectable gears, linkages, bars, tubes, and/or cables, for example.

One or more of sensors 2008, for example, provide real-time feedback to the processor 2006 about one or more operational parameters monitored during a surgical procedure being performed by the surgical system 2002. The operational parameters can be associated with a user performing the surgical procedure, a tissue being treated, and/or one or more components of the surgical system 2002, for example. The sensors 2008 may comprise any suitable sensor, such as, for example, a magnetic sensor, such as a Hall effect sensor, a strain gauge, an encoder, a position sensor, a force sensor, a pressure sensor, an inductive sensor, such as an eddy current sensor, a resistive sensor, a capacitive sensor, an optical sensor, and/or any other suitable sensor.

Further to the above, in various arrangements, the sensors 2008 may comprise any suitable sensor for detecting one or more conditions at the end effector 2010 including, without limitation, a tissue thickness sensor such as a Hall Effect Sensor or a reed switch sensor, an optical sensor, a magneto-inductive sensor, a force sensor, a pressure sensor, a piezo-resistive film sensor, an ultrasonic sensor, an eddy current sensor, an accelerometer, a pulse oximetry sensor, a temperature sensor, a sensor configured to detect an electrical characteristic of a tissue path (such as capacitance or resistance), or any combination thereof. As another example, and without limitation, the sensors 2008 may include one or more sensors located at, or about, an articulation joint extending proximally from the end effector 2010. Such sensors may include, for example, a potentiometer, a capacitive sensor (slide potentiometer), piezo-resistive film sensor, a pressure sensor, a pressure sensor, or any other suitable sensor type. In some arrangements, the sensor 2008 may comprise a plurality of sensors located in multiple locations in the end effector 2010.

In accordance with the present disclosure, the surgical system 2002 may include a feedback system 2013 which may include one or more devices for providing a sensory feedback to a user. Such devices may comprise, for example, visual feedback devices (e.g., an LCD display screen, a touch screen, LED indicators), audio feedback devices (e.g., a speaker, a buzzer) or tactile feedback devices (e.g., haptic actuators).

The microcontroller 2005 may be programmed to perform various functions such as precise control over the speed and position of the drive assembly 2011. In accordance with the present disclosure, the microcontroller 2005 may be any single-core or multicore processor such as those known under the trade name ARM Cortex by Texas Instruments. Additionally, the main microcontroller 2005 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHZ, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

The microcontroller 2005 may be configured to compute a response in the software of the microcontroller 2005. The computed response is compared to a measured response of the actual system to obtain an "observed" response, which is used for actual feedback decisions. The observed response is a favorable, tuned value that balances the smooth, continuous nature of the simulated response with the measured response, which can detect outside influences on the system.

The motor assembly 2009 includes one or more electric motors and one or more motor drivers. The electric motors can be in the form of a brushed direct current (DC) motor with a gearbox and mechanical links to the drive assembly 2011. In accordance with the present disclosure, a motor driver may be an A3941 available from Allegro Microsystems, Inc.

In accordance with the present disclosure, the motor assembly 2009 may include a brushed DC driving motor having a maximum rotational speed of approximately 25,000 RPM. The motor assembly 2009 may include a brushless motor, a synchronous motor, a stepper motor, or any other suitable electric motor. The motor driver may comprise an H-bridge driver comprising field-effect transistors (FETs), for example.

The motor assembly 2009 can be powered by a power source 2012. In accordance with the present disclosure, the power source 2012 may include one or more batteries which may include a number of battery cells connected in series that can be used as the power source to power the motor assembly 2009. Further, in accordance with the present disclosure, the battery cells of the power assembly may be replaceable and/or rechargeable. Additionally, the battery cells may comprise lithium-ion batteries which can be couplable to and separable from the power assembly.

Further to the above, the end effector 2010 includes a first jaw 2001 and a second jaw 2003. At least one of the first jaw 2001 and the second jaw 2003 is rotatable relative to the other during a closure motion that transitions the end effector 2010 from an open configuration toward a closed configuration. In accordance with the present disclosure, a cartridge jaw can be movable relative to a fixed anvil jaw to a clamped position. Additionally, an anvil jaw can be movable relative to a fixed cartridge jaw to a clamped position. Furthermore, an anvil jaw and a cartridge jaw may both be movable relative to each other to a clamped position. The closure motion may cause the jaws 2001, 2003 to grasp tissue therebetween. In accordance with the present disclosure, sensors, such as, for example, a strain gauge or a microstrain gauge, can be configured to measure one or more parameters of the end effector 2010, such as, for example, the amplitude of the strain exerted on the one or both of the jaws 2001, 2003 during a closure motion, which can be indicative of the closure forces applied to the jaws 2001, 2003. The measured strain can be converted to a digital signal and provided to the processor 2006, for example. Alternatively, additionally, sensors such as, for example, a load sensor, can measure a closure force and/or a firing force applied to the jaws 2001, 2003.

In accordance with the present disclosure, a current sensor can be employed to measure the current drawn by a motor of the motor assembly 2009. The force required to advance the drive assembly 2011 can correspond to the current drawn by the motor, for example. The measured force can be converted to a digital signal and provided to the processor 2006.

In accordance with the present disclosure, strain gauge sensors can be used to measure the force applied to the tissue by the end effector 2010, for example. A strain gauge can be coupled to the end effector 2010 to measure the force on the tissue being treated by the end effector 2010. Additionally, the strain gauge sensors can measure the amplitude or magnitude of the strain exerted on a jaw of an end effector 2010 during a closure motion which can be indicative of the tissue compression. The measured strain can be converted to a digital signal and provided to a processor 2006.

The measurements of the tissue compression, the tissue thickness, and/or the force required to close the end effector on the tissue, as respectively measured by the sensors 2008 can be used by the microcontroller 2005 to characterize the selected position of one or more components of the drive assembly 2011 and/or the corresponding value of the speed of one or more components of the drive assembly 2011. In accordance with the present disclosure, a memory (e.g. memory 2007) may store a technique, an equation, and/or a look-up table which can be employed by the microcontroller 2005 in the assessment.

The system 2002 may comprise wired or wireless communication circuits to communicate with surgical hubs (e.g. surgical hub 2014), communication hubs, and/or robotic surgical hubs, for example. Additional details about suitable interactions between a system 2002 and the surgical hub 2014 are disclosed in U.S. patent application Ser. No. 16/209,423 entitled METHOD OF COMPRESSING TISSUE WITHIN A STAPLING DEVICE AND SIMULTANEOUSLY DISPLAYING THE LOCATION OF THE TISSUE WITHIN THE JAWS, now U.S. Patent Application Publication No. 2019/0200981, the entire disclosure of which is incorporated by reference in its entirety herein.

In accordance with the present disclosure the control circuit 2004 can be configured to implement various processes described herein. The control circuit 2004 may comprise a microcontroller comprising one or more processors (e.g., microprocessor, microcontroller) coupled to at least one memory circuit. The memory circuit stores machine-executable instructions that, when executed by the processor, cause the processor to execute machine instructions to implement various processes described herein. The processor may be any one of a number of single-core or multicore processors known in the art. The memory circuit may comprise volatile and non-volatile storage media. The processor may include an instruction processing unit and an arithmetic unit. The instruction processing unit may be configured to receive instructions from the memory circuit of this disclosure.

Alternatively, in accordance with the present disclosure, the control circuit 2004 can be in the form of a combinational logic circuit configured to implement various processes described herein. The combinational logic circuit may comprise a finite state machine comprising a combinational logic configured to receive data, process the data by the combinational logic, and provide an output.

Alternatively, in accordance with the present disclosure, the control circuit 2004 can be in the form of a sequential logic circuit. The sequential logic circuit can be configured to implement various processes described herein. The sequential logic circuit may comprise a finite state machine. The sequential logic circuit may comprise a combinational logic, at least one memory circuit, and a clock, for example. The at least one memory circuit can store a current state of the finite state machine. In accordance with the present disclosure, the sequential logic circuit may be synchronous or asynchronous. Further, in accordance with the present disclosure, the control circuit 2004 may comprise a combination of a processor (e.g., processor 2006) and a finite state machine to implement various processes herein. Additionally, the finite state machine may comprise a combination of a combinational logic circuit (and the sequential logic circuit, for example.

Figure 3:
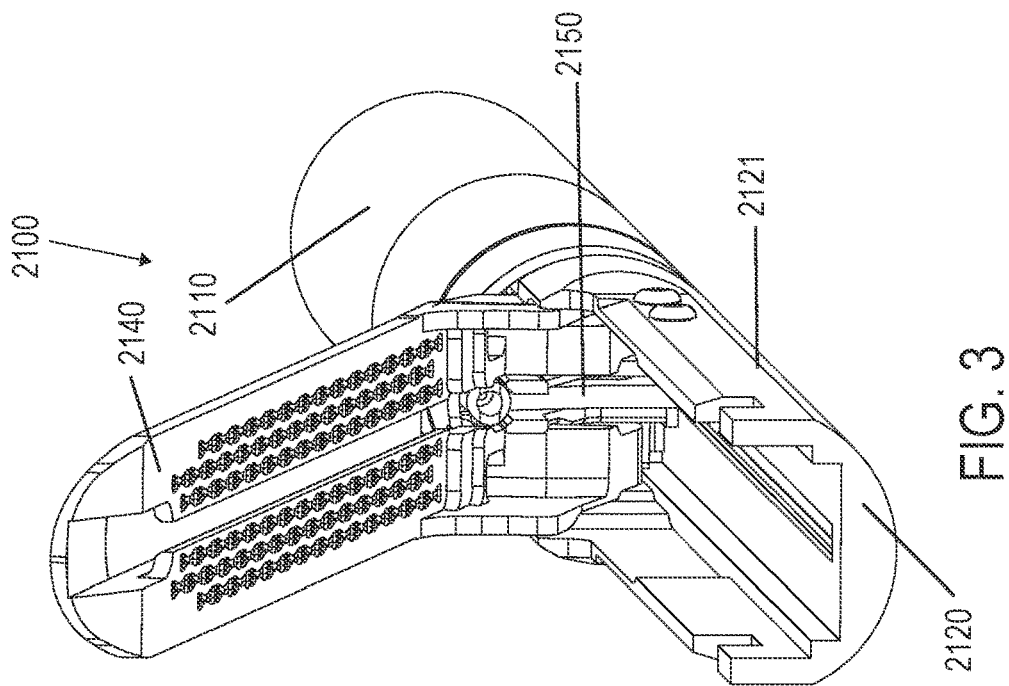
FIG. 3 is a partial perspective view of the surgical stapling end effector of FIG. 2, wherein the surgical stapling assembly comprises a shaft, a first jaw, and a second jaw movable relative to the first jaw to clamp tissue therebetween.
Figure 2:
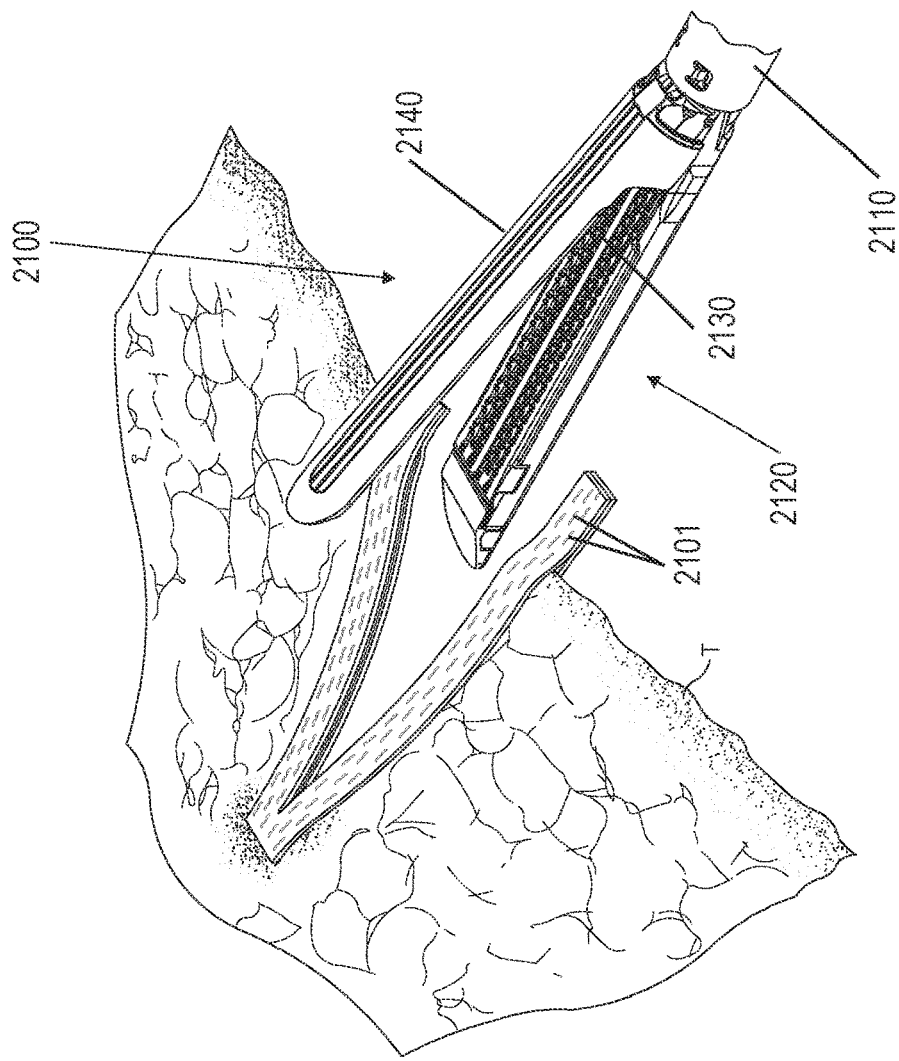
FIG. 2 is a partial perspective view of a surgical stapling assembly and tissue stapled and cut by the surgical stapling assembly, in accordance with the present disclosure.

FIGS. 2 and 3 depict a surgical stapling assembly 2100 configured to clamp, staple, and cut patient tissue T during a surgical stapling procedure. As discussed herein, one or more functions of the surgical stapling assembly 2100 can be motor-driven. The surgical stapling assembly 2100 comprises a shaft 2110 and an end effector 2120 extending from the shaft 2110. The end effector 2120 comprises a cartridge channel jaw 2121 and an anvil jaw 2140 movable relative to the cartridge channel jaw 2121 to clamp tissue therebetween during a clamping stroke. In accordance with the present disclosure, the cartridge channel jaw 2121 can be movable in addition to, or in lieu of, the anvil jaw 2140. The end effector 2120 further comprises a replaceable staple cartridge 2130 configured to be installed into the cartridge channel jaw 2121. The replaceable staple cartridge 2130 comprises a plurality of staples 2101 removably stored therein and configured to be ejected from the replaceable staple cartridge 2130 during a staple firing stroke. In accordance with the present disclosure, the staple cartridge 2130 may not be replaceable. A disposable loading unit may comprise a shaft and an end effector attachable to a control interface. Additionally, in accordance with the present disclosure, the entire cartridge channel jaw 2121 may be replaceable.

The surgical stapling assembly 2100 further comprises a firing driver 2150 actuatable through the end effector 2120 by a drive assembly such as the drive assembly 2011, for example. The firing driver 2150 can comprise any suitable firing driver such as, for example, a distal I-beam head, discussed in greater detail below. The firing driver 2150 is configured to push a sled of the replaceable staple cartridge 2130 from an unfired position to a fired position. During distal translation of the sled within the replaceable staple cartridge 2130, the sled is configured to sequentially lift a plurality of staple drivers with staples 2101 supported thereon. As the drivers are lifted toward the anvil jaw 2140, the drivers are configured to eject the staples 2101 from a plurality of staple cavities and against the anvil jaw 2140.

In accordance with the present disclosure, the sled can be part of the firing driver. Any suitable combination of firing components can be considered the firing driver.

In accordance with the present disclosure, moving the anvil jaw 2140 into a clamped position to clamp tissue between the anvil jaw 2140 and the replaceable staple cartridge 2130 may be performed by a closure driver. The closure driver may be separate from the firing driver 2150 and may be actuatable independently of the firing driver. Alternatively, the closure driver may not be separate from the firing driver 2150, and the clamping, or closing, motion may be performed by the firing driver 2150. Opposing jaw-camming pins of a distal I-beam head of the firing driver 2150 are configured to cam the anvil jaw 2140 into a clamped position as the firing driver 2150 is actuated distally through an initial clamping stroke, or motion. In addition to moving the anvil jaw 2140 from an unclamped position to a clamped position during a clamping stroke, the opposing jaw-camming pins are configured to control a tissue gap distance between the anvil jaw 2140 and the replaceable staple cartridge 2130 during the staple firing stroke by limiting the separation of the cartridge channel jaw 2121 and the anvil jaw 2140 during the staple firing stroke with the opposing jaw-camming pins. One of the jaw-camming pins is configured to engage the cartridge channel jaw 2121 and one of the jaw-camming pins is configured to engage the anvil jaw 2140. Discussed in greater detail herein, this clamping action provided by the opposing jaw-camming pins induces clamping forces on the firing driver 2150 and other drive components.

In accordance with the present disclosure, many different forces can be transmitted through the surgical stapling assembly 2100 and these forces can induce loads on the firing driver 2150. These loads can include, but are not limited to, jaw-camming loads experienced during the staple firing stroke as a result of the interaction between the jaws 2121, 2140 and the jaw-camming pins of the firing driver 2150, tissue loads experienced during the staple firing stroke as a result of the interaction between a cutting edge, or knife, of the firing driver 2150 or firing assembly generally, for example, and the patient tissue T, and/or staple firing loads experienced during the staple firing stroke as a result of the firing of the staples 2101 by the firing driver 2150. In accordance with the present disclosure, these loads experienced by the firing driver 2150 can be transmitted through the drive assembly, or drive train, which drives the firing driver 2150, to the prime mover of the drive train such as the motor, for example.

The loads experienced by the firing driver 2150 can affect the overall performance of the staple firing stroke performed by the surgical stapling assembly 2100. Various components of a drive assembly are provided which, in accordance with the present disclosure, may be utilized in a surgical stapling drive assembly to help increase the efficiency, control, and/or reliability, for example, of a surgical stapling drive stroke.

In accordance with the present disclosure, one or more components of the drive assembly, or drive train, may be designed so as to optimize one or more characteristics of the drive train for a drive stroke such as, for example, a surgical stapling drive stroke. Such characteristics may include inertial mass and/or storable kinetic energy, for example. These characteristics can be utilized by a control circuit (e.g., control circuit 2004) to further optimize the drive stroke, as discussed in greater detail below.

Figure 4:
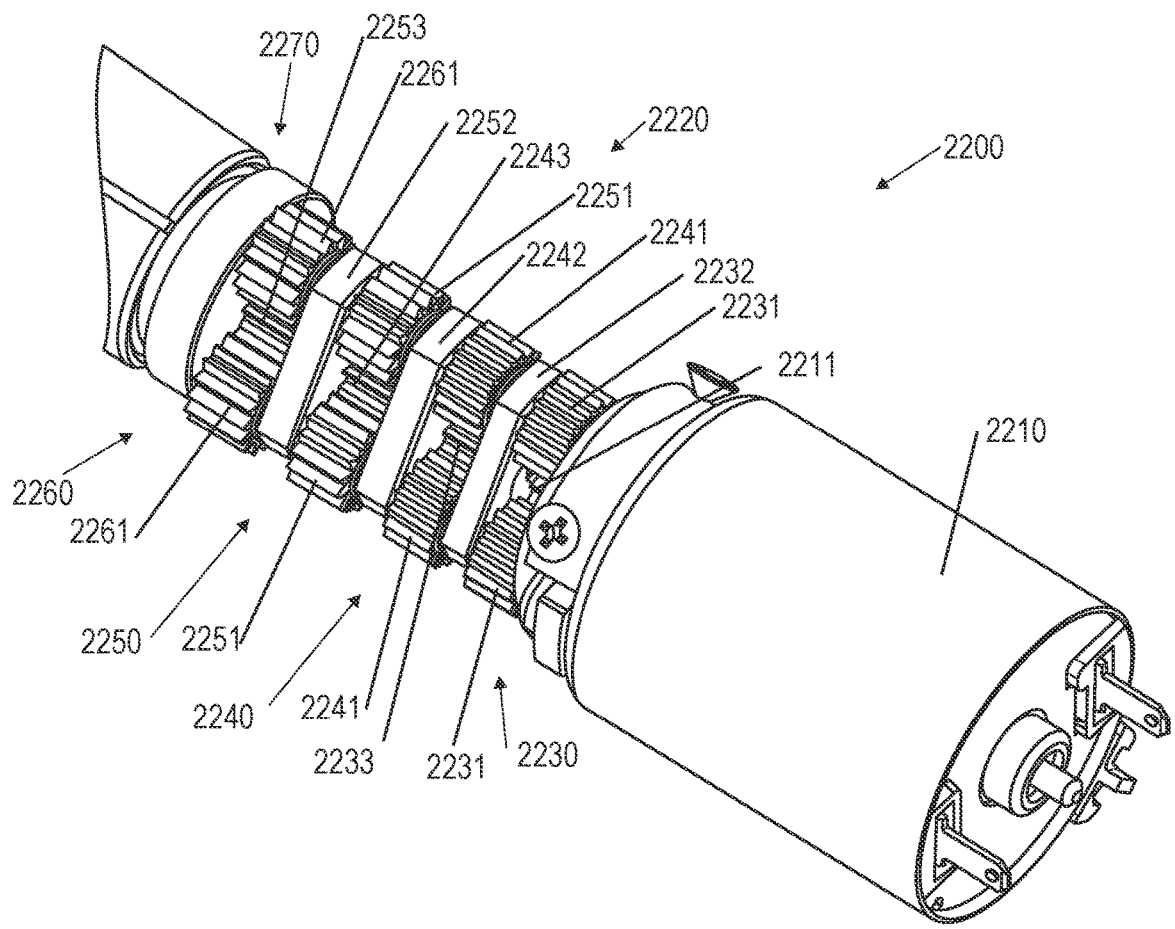
FIG. 4 is a perspective view of a drive assembly for use with a surgical stapling assembly, wherein the drive assembly comprises a motor, a drive train, and an output, in accordance with the present disclosure.
Figure 5:
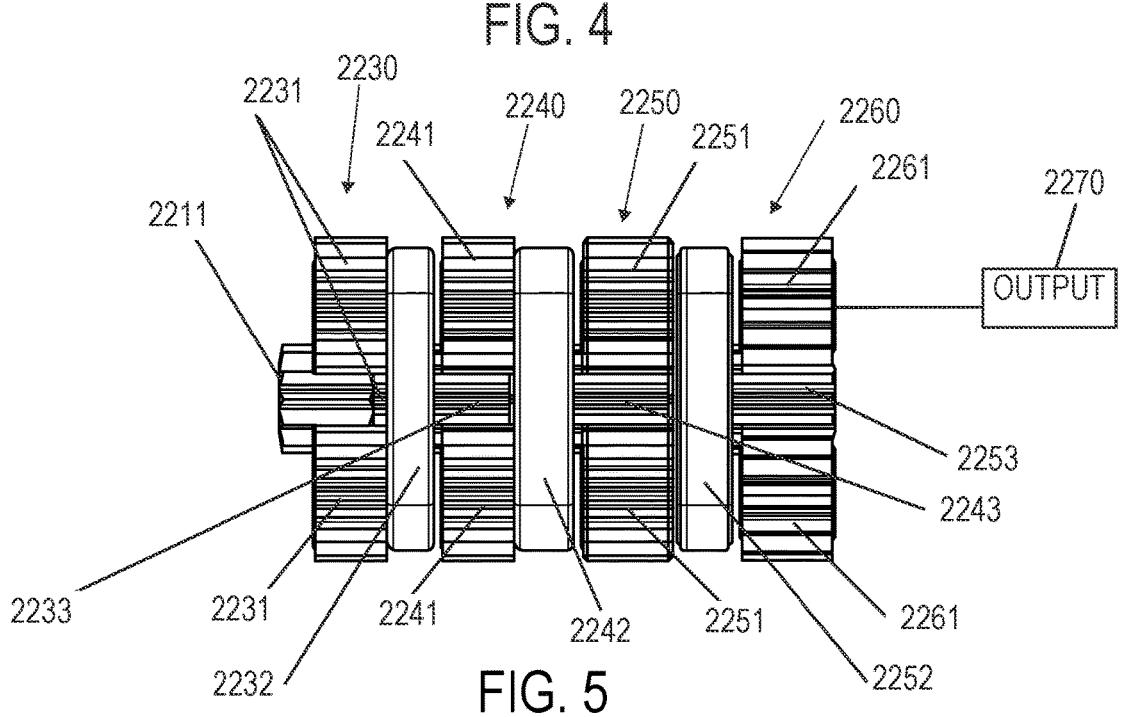
FIG. 5 is an elevational view of the drive train of FIG. 4.
Figures 6, 7:
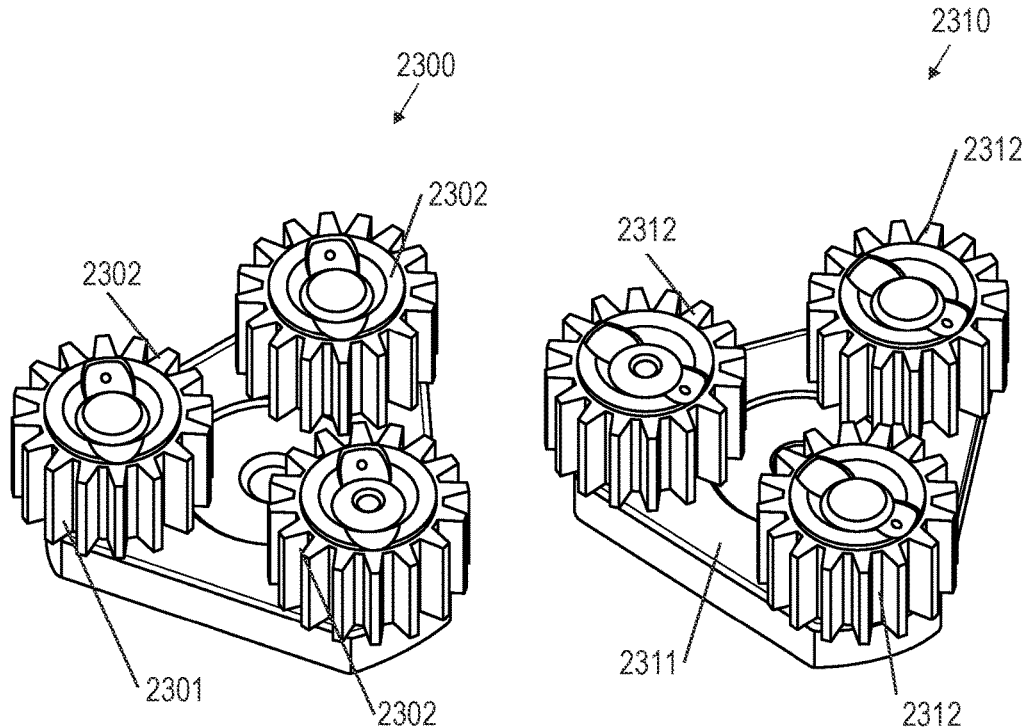
FIG. 6 is a perspective view of a gear stage for use with a gear train of a surgical instrument drive assembly, wherein the gear stage comprises a carrier and a plurality of planet gears rotatably mounted to the carrier, in accordance with the present disclosure.
FIG. 7 is a perspective view of a gear stage for use with a gear train of a surgical instrument drive assembly, wherein the gear stage comprises a carrier and a plurality of planet gears rotatably mounted to the carrier, in accordance with the present disclosure.

FIGS. 4 and 5 depict a drive assembly 2200 for use with a surgical stapling assembly such as the surgical stapling assembly 2100, for example. In accordance with the present disclosure, the drive assembly 2200 may be coupled to and configured to drive the firing driver 2150 through a drive stroke. The firing driver 2150 may comprise a firing beam having a first jaw-camming portion and a second jaw-camming portion. Additionally, the drive assembly 2200 may be controlled by a control circuit such as those described herein. The drive assembly 2200 comprises a motor 2210 and a gear train 2220 driven by the motor 2210. The drive assembly 2200 is configured to drive an output 2270. In accordance with the present disclosure, the output 2270 may be couplable to the firing driver 2150, for example. Any suitable drive driver can be coupled to the drive assembly 2200. The motor 2210 may comprise any suitable type of motor such as, for example, an electric motor. The motor 2210 may comprise a brushed or brushless DC motor. The drive stroke may comprise an initial clamping stroke to approximate the jaws and, subsequently, a staple firing stroke to staple and cut tissue. Alternatively, the drive stroke may only comprise a staple firing stroke to staple and cut tissue.

The motor 2210 comprises an output pinion gear 2211 driven by the motor 2210 and configured to impart drive motions to the gear train 2220. The gear train 2220 comprises a plurality of gear sets 2230, 2240, 2250, and 2260. The first gear set 2230 comprises a plurality of input planet gears 2231 meshed with the output pinion gear 2211, a carrier 2232 by which the input planet gears 2231 are supported, and an output gear 2233 supported by the carrier 2232. The output pinion gear 2211 is meshed with and configured to drive the planet gears 2231 which are directly coupled to the carrier 2232. Thus, the planet gears 2231, the carrier 2232, and the output gear 2233 all rotate together when driven by the output pinion gear 2211. The second gear set 2240 comprises a plurality of input planet gears 2241 meshed with the output gear 2233, a carrier 2242 by which the input planet gears 2241 are supported, and an output gear 2243 supported by the carrier 2242. The output gear 2233 is meshed with and configured to drive the planet gears 2241 which are directly coupled to the carrier 2242. Thus, the planet gears 2241, the carrier 2242, and the output gear 2243 all rotate together when driven by the output gear 2233. The third gear set 2250 comprises a plurality of input planet gears 2251 meshed with the output gear 2243, a carrier 2252 by which the input planet gears 2251 are supported, and an output gear 2253 supported by the carrier 2252. The output gear 2243 is meshed with and configured to drive the planet gears 2251 which are directly coupled to the carrier 2252. Thus, the planet gears 2251, the carrier 2252, and the output gear 2253 all rotate together when driven by the output gear 2243. The output gear set 2260 comprises a plurality of planet gears 2261 meshed with the output gear 2253. The output gear set 2260 is configured to drive the output 2270 to drive a drive driver such as, for example, the firing driver 2150.

Any suitable gear ratio or ratios can be employed within the gear train 2220. In accordance with the present disclosure, each gear stage may employ between about a 5:1 and a 10:1 gear ratio, for example. Each gear stage may reduce the output speed by about 5:1, 6:1, and/or 7:1, for example. In accordance with the present disclosure, if the input speed of the motor 2210 is 20,000 RPM, for example, the output speed of the output 2270 may be reduced by 5:1 at each gear stage. Multiple gear stages can provide a compound gear ratio. Additionally, a lesser gear ratio may be utilized closer to the motor 2210 so as to conserve rotational speed at the first gear stage from the motor 2210. Further, in accordance with the present disclosure, greater gear ratios which are different than the lesser gear ratio can be used downstream of the motor 2210 so as to reduce the speed of the output 2270 as desired. Discussed in greater detail below, the conservation of rotational speed of the gear set(s) closer to the motor 2210 increases the ability of the drive train 2220 to produce and conserve angular momentum to overcome possible stall conditions, as discussed in greater detail below. In accordance with the present disclosure, output speed and/or torque of the output 2270 may be controlled by a motor control circuit (e.g., control circuit 2004) by varying input voltage and/or current to the motor 2210. Load on the motor 2210 can be monitored and utilized to further control the motor 2210.

In accordance with the present disclosure, gear trains for various surgical instruments can include any number of suitable number of gear stages. A surgical stapling assembly, such as the surgical stapling assembly 2100, for example, can include three gear stages and can complete a full firing stroke (about 2.5 inches, for example) in about three seconds with a load up to about 200 lbs. Alternatively, a circular surgical stapler can include five gear stages, and can complete a full firing stroke (about 0.5 inches, for example) in about 2-5 seconds with a load up to about 600 lbs. The number of gear stages may depend on the required firing load, duration of stroke, and/or length of stroke, for example. As the firing load increases during a firing stroke, the potential for motor stall increases. Increasing the inertial properties of one or more of the gear stages can increase the amount of momentum generated during the firing stroke in the gear train and, under potential stall-inducing loads, can help the gear train push through the potential stall-inducing loads without stalling. In accordance with the present disclosure, the gear stage which rotates with the highest speed (closest to the motor, for example) can be modified so as to increase the inertial properties thereof and, because inertia is proportional to the mass and rotational velocity of the gear stage, the gear stage closest to the motor can provide the most momentum within the gear train.

In accordance with the present disclosure, a housing ring gear may be employed with the drive assembly 2200. Such a housing ring gear can be fixed relative to the gear sets 2230, 2240, 2350, and 2260 and meshed with the planet gears 2231, 2241, 2251, and 2261. In accordance with the present disclosure, a shiftable gear may be provided to switch between different gears during a staple firing stroke.

In accordance with the present disclosure, the first gear set 2230 may spin at a rotational speed faster than all of the subsequent gear sets. Furthermore, the first gear set 2230 may comprise increased inertial properties such as for example, inertial mass and moment arms, relative to subsequent gear sets so as to increase the amount of rotational kinetic energy, or angular momentum, produced by the first gear set 2230. Discussed in greater detail below, the material selection and geometry of each individual gear set can be selected based on the location of the gear set relative to the output 2270 and/or the motor 2210 and/or based on the nominal rotational speed of the gear set determined by the gear ratio relative to the motor 2210. In accordance with the present disclosure, materials and/or geometries of one or more gear sets rotating with a greater velocity closer to the motor 2210 may be selected so as to prioritize the generation and/or storability of kinetic energy within the gear sets positioned closer to the motor 2210. Further, in accordance with the present disclosure, materials and/or geometries of one or more gear sets rotating with a lesser velocity further downstream of the motor 2210 may be selected so as to prioritize manufacturing costs and/or loading properties, for example. Additionally, one or more gear sets further downstream in the gear train 2220 may be comprised of plastic while one or more gear sets closer to the motor 2210 may be comprised of metal.

Turning now to FIGS. 6-9, different gear sets 2300 (FIG. 6), 2310 (FIG. 7), 2320 (FIG. 8), and 2330 (FIG. 9) are illustrated. In accordance with the present disclosure, each gear set 2300, 2310, 2320, 2330 may comprise materials, geometries, and/or components with different masses, sizes, and/or geometries thus changing the inertial properties of each gear set 2300, 2310, 2320, 2330. The drive assemblies disclosed herein may employ any combination of the gear sets 2300, 2310, 2320, and 2330. The combination of gear sets selected for a drive assembly can impact the overall inertial properties of the drive assembly. Each gear set may have specific inertial properties optimized for a surgical stapling drive stroke. Further, the inertial properties of each gear set may be selected based on the relative position of the gear set within a gear train.

In accordance with the present disclosure, the inertial properties may be selected based on a nominal operating speed of the gear set. As discussed above, a gear set having the greatest inertia may be selected for the first gear set coupled to the motor 2210 so as to generate a greater amount of kinetic energy with the fastest spinning gear set. For example, the gear set(s) closer to the motor 2210 can be driven at higher speeds than the gear sets further downstream of the motor 2210. Because of the higher nominal operating speed of the gear sets closer to the motor, these gear sets can include materials and design features so as to increase their inertial mass. Increasing the inertial mass of the faster-spinning gear sets can be employed to increase the overall inertia of the drive assembly 2200. The gear sets further downstream from the motor 2210 may be spun at lower nominal operating speeds and thus, increasing their inertial mass may minimally increase the overall inertia of the drive assembly 2200. In accordance with the present disclosure, all of the gear sets may be designed so as to increase the overall inertia of the drive assembly 2200. Additionally, the gear sets operating at lower nominal operating speeds may be selected so as to reduce manufacturing costs and/or reduce load properties.

The gear set 2300 comprises a carrier 2301 and planet gears 2302 rotatably mounted to the carrier 2301. In accordance with the present disclosure, a first material may be utilized for the carrier 2301 and a second material different than the first material may be utilized for the planet gears 2302. The first material may be lighter, as represented by mass in a given volume, than the second material. In accordance with the present disclosure, the first material may comprise a metal material and the second material may comprise a plastic material.

The gear set 2310 comprises a carrier 2311 and planet gears 2312 rotatably mounted to the carrier 2311. In accordance with the present disclosure, the carrier 2311 and the planet gears 2312 may comprise the same material. The material of the carrier 2311 and the planet gears 2312 may comprise a plastic material. Additionally, the inertial mass of the gear set 2300 may be more than the inertial mass of the gear set 2310.

The gear set 2320 comprises a carrier 2321 and planet gears 2322 rotatably mounted to the carrier 2321. In accordance with the present disclosure, the material of the carrier 2321 may comprise a plastic material. The material of the planet gears 2322 may comprise a hybrid material including at least two different materials. One of the materials may comprise tungsten. Additionally, the inertial mass of the gear set 2320 may be more than the inertial mass of the gear sets 2300, 2310. While plastic materials and metal materials are provided as examples of suitable materials for varying inertial mass of various components of the drive assembly 2200. It is readily understood that any suitable materials with different densities can be utilized.

Figures 8, 9:
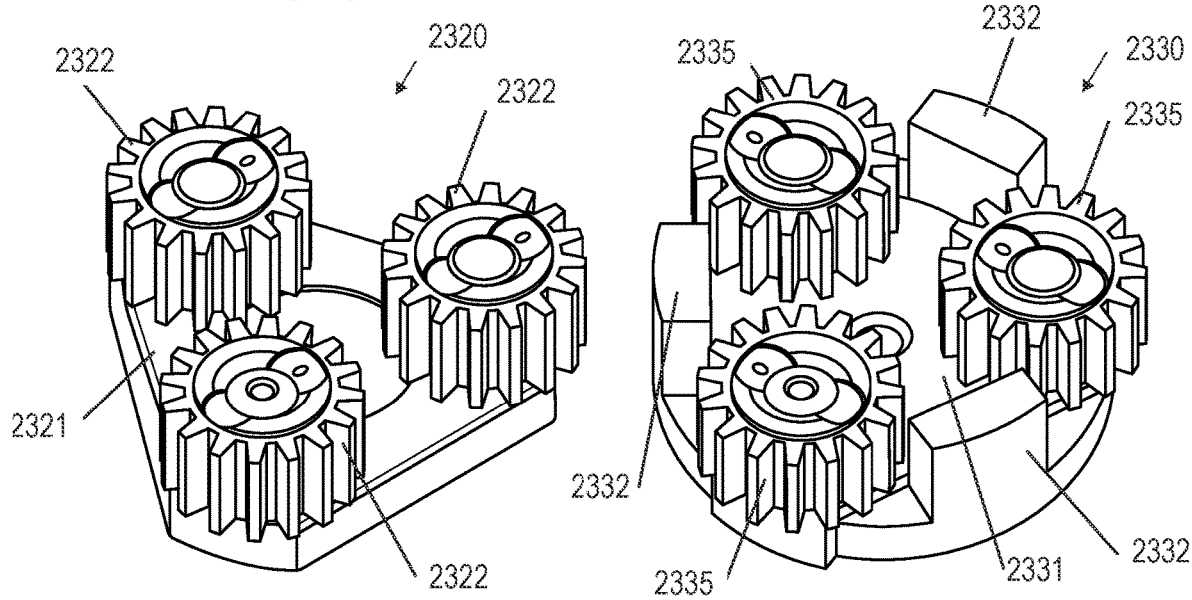
FIG. 8 is a perspective view of a gear stage for use with a gear train of a surgical instrument drive assembly, wherein the gear stage comprises a carrier and a plurality of planet gears rotatably mounted to the carrier, in accordance with the present disclosure.
FIG. 9 is a perspective view of a gear stage for use with a gear train of a surgical instrument drive assembly, wherein the gear stage comprises a carrier and a plurality of planet gears rotatably mounted to the carrier, and wherein the carrier comprises carrier posts positioned between each planet gear to increase the inertial properties of the gear stage, in accordance with the present disclosure.
Figure 11:
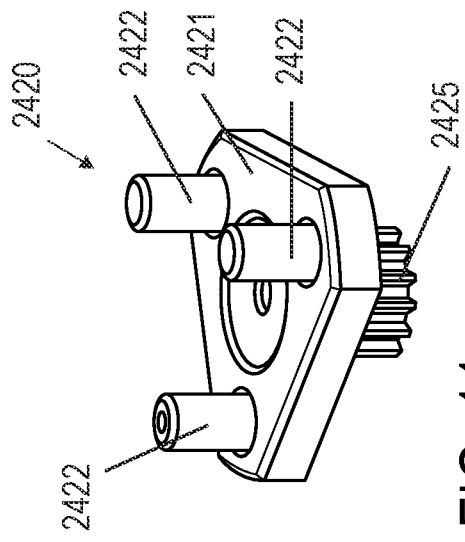
FIG. 11 is a perspective view of a carrier for use with a gear stage, wherein the carrier comprises mounting posts for rotatably supporting planet gears thereon and a pinion configured to drive a subsequent gear stage, in accordance with the present disclosure.

The gear set 2330 comprises a carrier 2331 and planet gears 2335 rotatably mounted to the carrier 2331. As can be seen in FIG. 9, the carrier 2331 comprises outer pillars 2332. In accordance with the present disclosure, the outer pillars 2332 may further increase the inertial mass of the carrier 2331 as compared to the carriers without the outer pillars 2332. The material of the carrier 2331 may comprise multiple materials such as, for example, metal and plastic materials, where a central portion of the carrier 2331 may comprise a plastic material and an outer portion of the carrier 2331 including the pillars 2332 may comprise a metal material. The material of the planet gears 2335 may comprise the same or different materials than the carrier 2331.

Referring still to FIG. 9, the mass of the carrier 2331 is increased and dispersed further outward to increase the storable kinetic energy of the carrier 2331. The size, mass, and/or location of the pillars 2332 can be specifically selected so as to increase the inertial properties of the carrier 2331 and, thus, the gear set 2330. In accordance with the present disclosure, the gear set 2330 may be the first gear set driven by the motor so as to rotate the gear set 2330 with the maximum rotational velocity in the gear train and, thus, generate a maximum amount of momentum within the gear train. Any of the carries disclosed herein may comprise any suitable shape such as triangular and/or circular, for example. The pillars 2332 may be situated closer to the perimeter of the carrier 2331 than the center of the carrier 2331 to increase the ability of the gear set 2330 to store kinetic energy.

Figure 13:
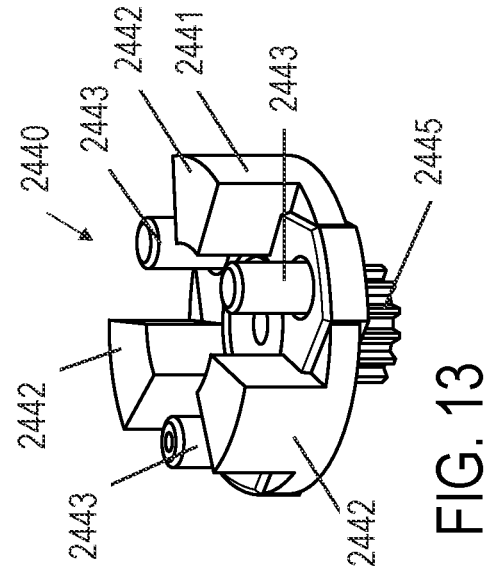
FIG. 13 is a perspective view of a carrier for use with a gear stage, wherein the carrier comprises mounting posts for rotatably supporting planet gears thereon and a pinion configured to drive a subsequent gear stage, and wherein the carrier further comprises secondary posts extending therefrom to increase the inertia of the carrier, in accordance with the present disclosure.
Figure 10:
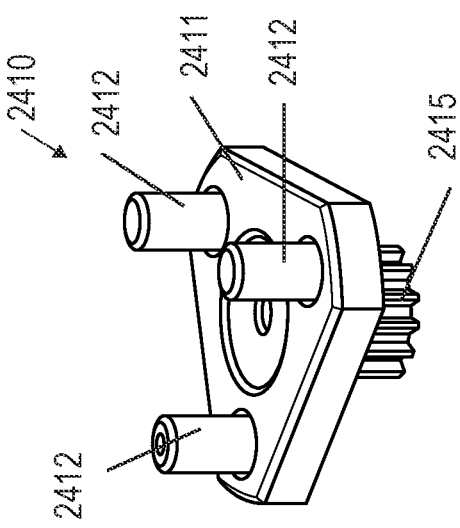
FIG. 10 is a perspective view of a carrier for use with a gear stage, wherein the carrier comprises mounting posts for rotatably supporting planet gears thereon and a pinion configured to drive a subsequent gear stage, in accordance with the present disclosure.
Figure 12:
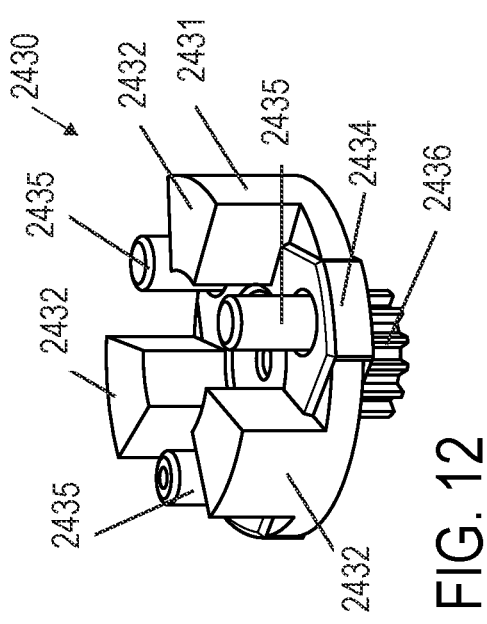
FIG. 12 is a perspective view of a carrier for use with a gear stage, wherein the carrier comprises mounting posts for rotatably supporting planet gears thereon and a pinion configured to drive a subsequent gear stage, and wherein the carrier further comprises secondary posts extending therefrom to increase the inertia of the carrier, in accordance with the present disclosure.

FIGS. 10-13 depict carriers 2410 (FIG. 10), 2420 (FIG. 11), 2430 (FIG. 12), and 2440 (FIG. 13). In accordance with the present disclosure, each carrier 2410, 2420, 2430, 2440 may comprise materials with different inertial masses and/or different geometries thus affecting the inertial properties thereof. The drive assemblies disclosed herein may employ any combination of the carriers 2410, 2420, 2430, and 2440 in a drive train thereof.

The carrier 2410 comprises a primary body portion 2411 and a pinion 2415 fixedly attached to the primary body portion 2411 such that the primary body portion 2411 and the pinion 2415 rotate together. The primary body portion 2411 comprises a plurality of mounting posts 2412 extending therefrom each of which is configured to rotatably support a planet gear thereon. The carrier 2410 comprises a first inertia value. In accordance with the present disclosure, the carrier 2410 may comprise a Nylon material, for example.

The carrier 2420 comprises a primary body portion 2421 and a pinion 2425 fixedly attached to the primary body portion 2421 such that the primary body portion 2421 and the pinion 2425 rotate together. The primary body portion 2421 comprises a plurality of mounting posts 2422 extending therefrom each of which are configured to rotatably support a planet gear thereon. The carrier 2420 comprises a second inertia value. In accordance with the present disclosure, the carrier 2420 can be cast with a steel material, for example. The first inertia value of the carrier 2410 may be less than the second inertia value of the carrier 2420.

The carrier 2430 comprises a primary body portion 2431, a secondary body portion 2434, and a pinion 930 fixedly attached to the primary body portion 2431 and the secondary body portion 2434 such that the primary body portion 2431, the secondary body portion 2434, and the pinion 2436 rotate together. The primary body portion 2431 comprises a plurality of secondary posts 2432 extending therefrom. In accordance with the present disclosure, the secondary posts 2432 can increase the inertial properties such as for example, the inertial mass, of the carrier 2430 relative to a carrier without secondary posts. The secondary body portion 2434 comprises a plurality of mounting posts 2435 each of which is configured to rotatably support a planet gear thereon. The carrier 2430 comprises a third inertia value.

In accordance with the present disclosure, the carrier 2430 may comprise a steel material and a Nylon material. The primary body portion 2431 may be cast with a steel material and the secondary body portion 2434 may comprise a Nylon material. The pinion 2436 may be part of the primary body portion 2431 and may also be made of a Nylon material. Alternatively, the pinion 2436 may be part of the secondary body portion 2434 and may also be cast with a steel material. Additionally, the third inertia value may be greater than the first inertia value of the carrier 2410 and the second inertia value of the carrier 2420.

The carrier 2440 comprises a body portion 2441 and a pinion 2445 fixedly attached to the body portion 2441 such that the body portion 2441 and the pinion 2445 rotate together. The body portion 2441 comprises a plurality of mounting posts 2443 extending therefrom and a plurality of secondary posts 2442 extending therefrom. In accordance with the present disclosure, the secondary posts 2442 can increase the inertial properties such as for example, the inertial mass, of the carrier 2440 relative to a carrier without secondary posts. Each mounting post 2443 is configured to rotatably support a planet gear thereon. The carrier 2440 comprises a fourth inertia value. The carrier 2440 can be entirely cast, or otherwise formed, with a steel material. Additionally, the fourth inertia value may be greater than the first inertia value of the carrier 2410, the second inertia value of the carrier 2420, and the third inertia value of the carrier 2430.

Figure 14:
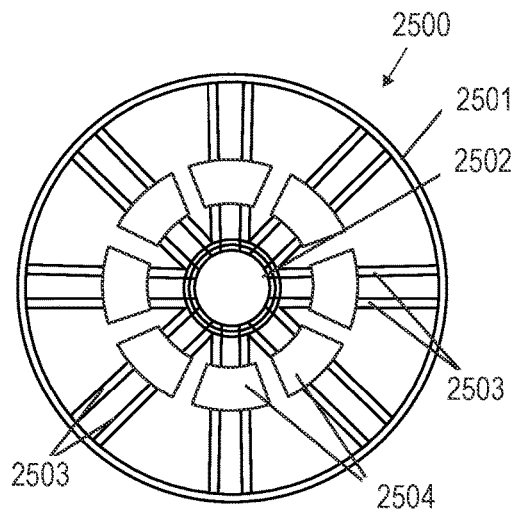
FIG. 14 is an elevational view of a variable flywheel for use with a drive assembly of a surgical instrument, wherein the variable flywheel comprises movable masses for varying the storable kinetic energy of a drive assembly, and wherein the masses are illustrated in a collapsed position, in accordance with the present disclosure.
Figure 15:
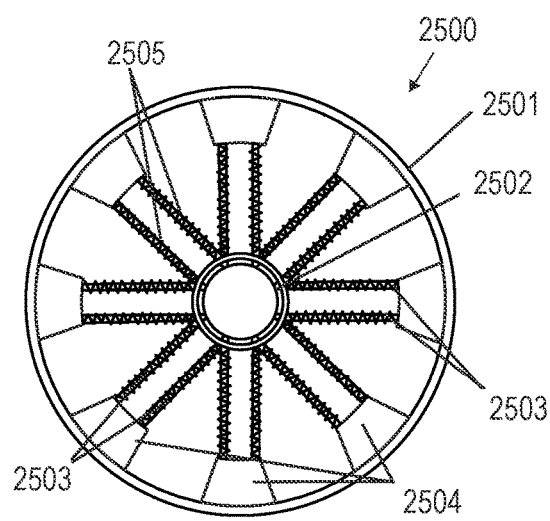
FIG. 15 is an elevational view of the variable flywheel of FIG. 14, wherein the masses are illustrated in an expanded position.

Various other components of a drive assembly 2200 can be selected for altering the inertial properties of the drive assembly of a surgical stapling device, for example. FIGS. 14-15 depict a flywheel, disc, or rotor, 2500 configured to increase the ability of a drive assembly for a surgical instrument to store rotational kinetic energy of a drive assembly by increasing the rotational inertia of the drive assembly. In accordance with the present disclosure, the flywheel 2500 may be mounted to a gear train (e.g., gear train 2220) within a drive assembly (e.g., drive assembly 2200) so as to increase the amount of storable kinetic energy during a drive stroke.

In accordance with the present disclosure, the flywheel 2500 may be passively actuated between a plurality of different configurations so as to provide different levels of inertia in each of the configurations. Alternatively, the flywheel 2500 may be actively actuated manually and/or automatically by a control circuit (e.g., control circuit 2004) between a plurality of different configurations so as to provide different levels of inertia. Additionally, the flywheel 2500 may be configured to utilize conservation of momentum to store rotational kinetic energy during a drive stroke.

The flywheel 2500 comprises an inner hub portion 2501, an outer rim portion 2502, and a plurality of struts, or arms, 2503 connecting the inner hub portion 2501 and the outer rim portion 2502. In accordance with the present disclosure, the inner hub portion 2501 can be mounted to a drive shaft of a drive assembly (e.g., drive assembly 2200). The flywheel 2500 can be mounted to the drive assembly near the motor before the gear box. Alternatively, the flywheel 2500 can be mounted to the drive assembly within the gear box. Additionally, the flywheel 2500 can be mounted to the drive assembly downstream, or distal, of the gear box.

The struts 2503 each comprise a radially-extending arm mounted to the inner hub portion 2501 and outer rim portion 2502 and can be oriented in a plurality of arm pairs. The flywheel 2500 further comprises masses 2504 slidably mounted to the struts 2503 such that the masses 2504 can be positioned near the inner hub portion 2501 as the flywheel 2500 rotates and the masses 2504 can be positioned near the outer rim portion 2502 as the flywheel 2500 rotates. The masses 2504 are configured to increase the rotational inertia of a drive assembly during a firing stroke by providing masses which are movable away from the center of rotation to increase the moment of inertia of the flywheel 2500 and, thus, the drive assembly.

In accordance with the present disclosure, the masses 2504 can be passively actuated between an inner position near the inner hub portion 2501 (FIG. 14) and an outer position near the outer rim portion 2502 (FIG. 15). In the illustrated example, springs 2505 are provided so as to hold the masses 2504 near the inner hub portion 2501 during little or no rotation of the flywheel 2500 but allow the masses 2504 to move radially outwardly toward the outer rim portion 2502 as the rotational velocity of the flywheel 2500 increases. This can reduce the amount of startup torque required by the motor of the drive assembly (e.g., drive assembly 2200) to initiate rotation the drive assembly but maximize rotational kinetic energy once the drive assembly is spinning at a nominal operating speed, for example.

In the instance of passive actuation of the masses 2504, the springs 2505 may comprise any suitable preselected spring constant selected so as to allow the masses 2504 to move radially outwardly as the flywheel 2500 increases rotational velocity to a nominal rotational velocity. During a decrease in velocity, the rotational kinetic energy stored in the flywheel 2500 is directed through, or released into, the drive assembly (e.g., drive assembly 2200) in an effort to reduce the possibility of a stall condition. As the speed of the flywheel 2500 decreases, the masses 2504 may be pulled back in closer to the inner hub portion 2504 to prepare for the next drive stroke by way of the springs 2505. In accordance with the present disclosure, the spring constant of the springs 2505 may be selected so as to control the position of the masses 2504 at different rotational speeds of the flywheel 2500. Further, in accordance with the present disclosure, the masses 2504 may not be pulled in closer to the inner hub portion 2504 until the flywheel 2500 fully stops rotating or nearly fully stops rotating, for example.

In accordance with the present disclosure, each spring 2505 may comprise a different spring constant so as to control the release of the masses 2504 toward the outer rim portion 2502. Such a configuration can allow for varied levels of inertia during a drive stroke. The different spring constants would require different rotational velocities of the flywheel 2500 to deploy each mass 2504 toward the outer rim portion 2502. In accordance with the present disclosure, the different rotational velocities required to deploy each mass to achieve a specific inertia level can be known and can be pursued by a control circuit (e.g., control circuit 2004) accordingly. For example, if a detected load on a motor is increasing at a predetermined rate that indicates a potential stall condition is imminent, the control circuit can be configured to automatically increase the rotational speed of the flywheel 2500 so as to generate more kinetic energy within the drive assembly. This additional kinetic energy can help push through the potential stall condition. If the load falls below a predetermined threshold after the potential stall condition is detected, the rotational speed of the flywheel 2500 can be reduced to move one or more masses 2504 back toward the inner hub portion 2501 and reduce the inertia level of the drive assembly when high stored kinetic energy is not necessary and, in accordance with the present disclosure, less desirable. If the kinetic energy stored in a drive assembly is too high, the magnitude of undershoot error and/or overshoot error of the drive stroke can increase. For example, a target velocity of a drive driver may be overshot and undershot by a larger margin with the unnecessary, increased stored kinetic energy than if the increased stored kinetic energy was not present in the drive assembly.

In accordance with the present disclosure, the masses 2504 can be actuated automatically by a control circuit (e.g., control circuit 2004) between the inner positions (FIG. 14) and the outer positions (FIG. 15). Additionally, a control circuit can automatically deploy one or more masses 2504 to their outer positions and/or inner positions to pursue the desired amount of stored kinetic energy in the drive assembly at any given time during the drive stroke. Any suitable actuation method can be utilized. A linear actuator such as a solenoid, for example, may be provided for each mass 2504 so as to be able to control each mass 2504 individually thereby providing several different levels of rotational inertia within the drive assembly.

Figure 16:
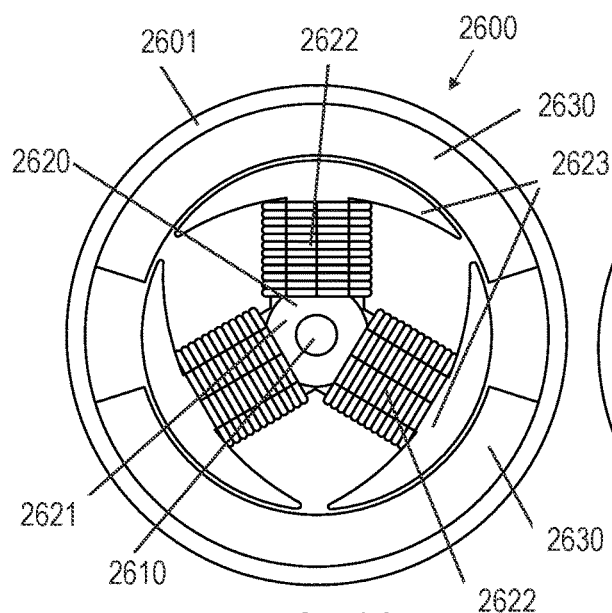
FIG. 16 is an cross-sectional view of a motor for use with a drive assembly of a surgical instrument, in accordance with the present disclosure.
Figure 17:
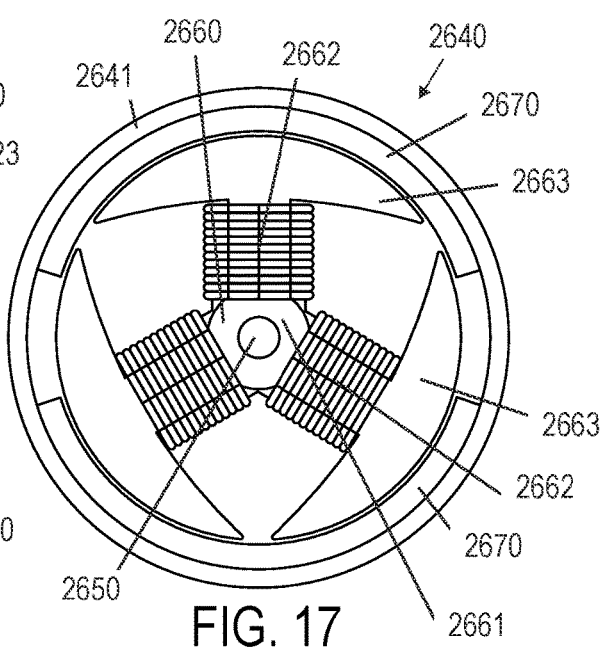
FIG. 17 is an cross-sectional view of a motor for use with a drive assembly of a surgical instrument, in accordance with the present disclosure.

FIGS. 16 and 17 depict different motor configurations configured to contribute different levels of inertia to a drive assembly. In accordance with the present disclosure, the motors illustrated in FIGS. 16 and 17 may comprise DC motors. The motors can be brushed or brushless. FIG. 16 depicts a motor 2600 comprising a motor housing 2601, an output shaft 2610, a rotor 2620 connected to the output shaft 2610, and stator magnets 2630 all housed within the motor housing 2601. The rotor 2620 comprises an inner hub portion 2621, coil winding arms 2622 extending outwardly from the inner hub portion 2621, and outer rotor extensions 2623 extending outwardly from the coil winding arms 2622.

FIG. 17 depicts a motor 2640 comprising a motor housing 2641, an output shaft 2650, a rotor 2660 connected to the output shaft 2650, and stator magnets 2670 all housed within the motor housing 2641. The rotor 2660 comprises an inner hub portion 2661, coil winding arms 2662 extending outwardly from the inner hub portion 2661, and outer rotor extensions 2663 extending outwardly from the coil winding arms 2662.

As can be seen in FIGS. 16 and 17, the outer rotor extensions 2663 comprise a larger volume than the outer rotor extensions 2623. In accordance with the present disclosure, the outer rotor extensions 2663 may comprise a greater mass and/or weight than the outer rotor extensions 2623. Similarly, the stator magnets 2630 may comprise a greater volume than the stator magnets 2670. The motor 2640 may have a greater inertia than the motor 2600. Additionally, the motor 2640 can be configured to generate and store more rotational kinetic energy for use within a surgical instrument drive assembly than the motor 2600.

Different inertial properties of components of a drive assembly can vary the ability of the drive assembly to store mechanical energy during a drive stroke within the drive assembly. In accordance with the present disclosure, more inertial mass of a gear stage of a gear box, for example, can increase the rotational kinetic energy of the drive assembly during a drive stroke. An inertial mass of one or more gear box components may be selected to provide sufficient kinetic energy during the drive stroke to overcome a stall condition of the motor caused by the external application of a predicted stall-induced load on the drive element. Additionally, increasing the moment arm of the planet gears of a gear stage can increase the inertia of the gear stage and, thus, the drive assembly. Increasing the mass of one or more of the planet gears can increase the inertia of the gear stage. This increase in rotational energy of a gear stage can result in an increased ability of the drive assembly to generate and/or conserve angular momentum. The increased ability to conserve angular momentum, or store rotational energy, can help reduce the possibility of motor stall, for example, discussed in greater detail below.

The drive assemblies and systems provided herein are configured to increase the amount of load absorbable within the system without stalling the motor. In accordance with the present disclosure, the increased inertial properties of the gear train may allow the systems to overcome force variations beyond a peak motor input torque (maximum torque available by the motor) owing to the stored kinetic energy in the system.

In accordance with the present disclosure, a control circuit (e.g., control circuit 2004) of a surgical instrument coupled to a motorized drive train which controls a drive stroke of the surgical instrument can utilize inertial characteristics of a drive train to help automatically reduce the likelihood of motor stall during the drive stroke.

In accordance with the present disclosure, the control circuit 2004 can be configured to monitor one or more parameters of the drive assembly during a drive stroke and the stored kinetic energy of the drive assembly in an effort to detect an imminent motor stall condition. The control circuit 2004 is configured to compare, or evaluate, the monitored one or more parameters and the stored kinetic energy of the drive assembly to determine if motor stall is imminent.

The parameters can include any suitable parameter or combination of parameters of the drive assembly. In accordance with the present disclosure, the parameters can include various motor parameters such as, for example, motor velocity, motor current, motor acceleration, motor load, motor efficiency, motor heat, and/or voltage sag, etc. The parameters can include various gear box parameters such as, for example, rotational velocity, rotational acceleration, and/or stored kinetic energy of one or more gear stages. Additionally, the parameters can include various aspects of a drive member, or driver, such as, for example, load on the drive member (which can be induced by stapling forces caused by ejecting staples from a staple cartridge and forming the staples against the anvil, clamping forces caused by clamping tissue between the jaws and/or controlling a tissue gap distance between the jaws during a staple firing stroke, and/or tissue-cutting forces caused by the interaction between a tissue-cutting knife of the drive member and the tissue during the staple firing stroke), velocity of the drive member, and/or acceleration of the drive member.

Any of the parameters or combination of parameters discussed herein can be utilized in determining that a motor stall event is imminent. A reduction in speed of the drive member, rapid deceleration of the drive member, and/or increased motor current and/or torque, for example, can all be signs of an imminent motor stall condition. A reduction in gear stage speed can also indicate motor stall is imminent. In accordance with the present disclosure, an increase in motor heat, motor torque, and/or motor current can indicate that a motor stall event is imminent. A combination of parameters may be monitored by the control circuit 2004 to detect an imminent motor stall condition. Additionally, more than one parameter of a drive assembly may be monitored and only when every monitored parameter indicates that a motor stall condition is imminent does the control circuit 2004 determine that a motor stall condition is imminent.

In accordance with the present disclosure, one or more of the parameters can be configured to be monitored over a period of time and analyzed to determine the rate at which the parameter is changing, for example. The rate of change of the parameters can be evaluated by the control circuit 2004 during a staple firing stroke and, when one or more particular parameters changes a predetermined amount, or at a predetermined threshold rate of change, over a predetermined period of time, the control circuit 2004 can utilize this information in determining an imminent motor stall condition. For example, if current increases rapidly at a predetermined threshold rate of increase, this can be utilized to determine that a motor stall condition is imminent.

In accordance with the present disclosure, the control circuit 2004 can detect an imminent motor stall condition based on multiple parameters, as discussed above. The control circuit 2004 may separately compare values, which can be determined based on sensor signals received from sensors that monitor such parameters, to a predetermined threshold associated with each parameter. Alternatively, the imminent motor stall condition can be a function of a number of parameters weighed diffidently in a predetermined equation for detecting the imminent motor stall condition.

As discussed herein, the control circuit 2004 is further configured to monitor and/or determine a kinetic energy stored in the drive assembly during a staple firing stroke, for example, to evaluate alongside, or compare with, the monitored parameter. If the determined stored kinetic energy of the drive assembly is below a predetermined kinetic energy threshold for a given stall condition, which would indicate that the motor is likely to stall unless an adjustment is made to the drive stroke, an adjustment can be made to the drive stroke in an effort to overcome the stall condition and completely prevent the motor from stalling. In accordance with the present disclosure, the adjustment can include making a motor adjustment which increases the kinetic energy of the drive assembly to push through, or overcome, the imminent stall condition.

The kinetic energy stored in the drive assembly can be determined in any suitable manner such as, for example, by monitoring the rotational speed of the motor and/or a particular gear stage, for example. In accordance with the present disclosure, the control circuit 2004 can calculate the kinetic energy stored in the drive assembly using the known values of drive assembly such as for example, the mass of the gear box components (planet gears and carriers), and a variable parameter (parameter which changes during the firing stroke) of the gear box component (speed of a particular gear stage). The control circuit 2004 can be configured to sum the kinetic energy storage of every component in the drive assembly to determine the total stored kinetic energy in the drive assembly at any given time during the firing stroke.

As the stored kinetic energy increases and decreases during the drive stroke, the ability of the drive assembly to overcome a stall condition increases and decreases. For example, if the drive member is moving relatively slowly during the drive stroke, a relatively low amount of stored kinetic energy can be present within the drive assembly. Therefore, the ability of the drive assembly to overcome a potential motor stall event decreases. Given this decrease in stored kinetic energy, the control circuit 2004 is configured to adjust the sensitivity of the trigger, or parameter, thresholds of the monitored parameters which would require, or trigger, a motor adjustment to overcome a stall condition. For example, as the stored kinetic energy of the drive assembly decreases, the tolerance for stall-related variations of the drive assembly is decreased because less kinetic energy is stored within the drive assembly lowering the ability of the drive assembly to overcome a stall condition. As another example, as the stored kinetic energy of the drive assembly increases, the tolerance for stall-related variations of the drive assembly is increased because more kinetic energy is stored within the drive assembly increasing the ability of the drive assembly to overcome a stall condition.

In accordance with the present disclosure, the control circuit 2004 can be further configured to utilize a kinetic energy threshold during a drive stroke. The kinetic energy threshold may be predetermined, or preset. Additionally, the kinetic energy threshold may be adjusted in real time by the control circuit 2004 during the drive stroke based on one or more parameters of the drive stroke. Different kinetic energy thresholds may be set for different stages of the drive stroke. The stages may include, for example, a lockout stage where an I-beam is either locked out or defeats the lockout as the I-beam moves through the lockout stage, an initial clamping stage where the I-beam engages opposing jaw-camming channels defined in the jaws as the jaws initially clamp on tissue, a tissue cutting and stapling stage where the I-beam ejects staples, cuts tissue, and holds the jaws clamped during the stapling and cutting of tissue, and/or an ending stage after the firing of staples.

The kinetic energy threshold can be preset for each stage corresponding to the anticipated stored kinetic energy which may be required to overcome a potential stall condition during each stage of the drive stroke. For example, the lockout stage may require a relatively low kinetic energy. This may be due to the fact that there is little-to-no jaw-camming forces acting on the I-beam pins, no cutting of tissue, and no stapling of tissue, for example. Thus, the likelihood of motor stall may be much less likely during the lockout stage of the drive stroke. Because motor stall is unlikely and/or because the load, for example, experienced during the lockout stage is low, a relatively low kinetic energy threshold can be set by the control circuit 2004 for the lockout stage.

In accordance with the present disclosure, the tissue cutting and stapling stage may involve the greatest loads on the drive assembly. In accordance with the present disclosure, a relative high kinetic energy threshold may be set to ensure that a maximum amount of available stored kinetic energy of the drive assembly is being provided during the tissue cutting and stapling stage so that, in the event of detecting a possible motor stall condition, a maximum amount of kinetic energy is stored in the drive assembly to overcome the motor stall condition.

In accordance with the present disclosure, the kinetic energy threshold may be utilized by the control circuit 2004 to ensure that the drive assembly is actuated to provide a stored kinetic energy which meets and/or exceeds the kinetic energy threshold during a particular stage of the drive stroke. The control circuit 2004 can be configured to compare the determined stored kinetic energy of the drive assembly with the kinetic energy threshold and initiate a motor control adjustment should the stored kinetic energy of the drive assembly fall below the kinetic energy threshold, for example, in an effort to maintain a stored kinetic energy that meets and/or exceeds the kinetic energy threshold.

In accordance with the present disclosure, a comparison of the kinetic energy threshold and the stored kinetic energy of the drive assembly may be utilized to adjust a sensitivity of one or more parameter thresholds indicative of motor stall. Such parameter thresholds are monitored parameter values of the drive stroke which may trigger a motor adjustment. The parameter thresholds may comprise a range of monitored parameter values where, for example, when the monitored parameter falls outside of the range, a motor adjustment is triggered. Alternatively, a parameter threshold may not comprise a range but, rather, a single value where, for example, when the monitored parameter exceeds, or falls below, the parameter threshold, a motor adjustment may be made. A motor adjustment may be made to, ultimately, prevent motor stall. This can be achieved by adjusting torque output of the motor, speed output of the motor, acceleration output of the motor, etc. For example, a motor adjustment may include increasing the speed of the motor to a maximum speed for a short duration in an effort to serve as a kinetic buffer during the potential stall event. In accordance with the present disclosure, the motor adjustment may be held until a stall condition is no longer detected. A multitude of quick speed bursts may be provided by the control circuit 2004 in an attempt to overcome the potential stall condition.

As discussed herein, the sensitivity, or tolerance, of the parameter threshold can be adjusted in real time based on the stored kinetic energy of a drive assembly during a drive stroke. In other words, with less stored, or storable, kinetic energy, a parameter threshold can be adjusted to be more sensitive such that a more marginal variation of the monitored parameter would trigger a motor adjustment. This can be a result of the greater stall risk associated with less stored, or storable, kinetic energy. Similarly, with more stored, or storable, kinetic energy, the parameter threshold can be adjusted to be less sensitive so that a greater variation of the monitored parameter is permitted prior to triggering a motor adjustment. This can be a result of the lower stall risk associated with more stored, or storable, kinetic energy. In accordance with the present disclosure, the sensitivity may be adjusted based on the amount of stored kinetic energy. Additionally, the sensitivity may be based on the comparison of the amount of stored kinetic energy at a given moment and the kinetic energy threshold.

For example, if the stored kinetic energy of the drive assembly is much greater than the kinetic energy threshold, the parameter threshold can be set a first, less conservative, sensitivity. If the stored kinetic energy of the drive assembly is much lower than the kinetic energy threshold, the parameter threshold can be set at a second, more conservative, sensitivity.

In accordance with the present disclosure, there may be increased risk of motor stall in a device without an adaptable sensitivity adjustment of the parameter thresholds. Assume the parameter threshold is not adjusted as the speed of the drive element, for example, varies through the drive stroke, and the parameter threshold is set at a 10% increase in load thereby initiating a motor adjustment at a 10% increase in load at any given drive element speed. Should the load increase 10%, a motor adjustment is made. This may be adequate at higher, more nominal drive element speeds, where a 10% increase in load may not necessarily stall the motor. However, at a lower speed, a 10% increase in load may cause a motor stall because of the lower storable kinetic energy. Thus, the control circuit (e.g., control circuit 2004) described herein would adjust the parameter threshold to a more sensitive load variation such as, for example, 5% at lower speeds. The parameter threshold may be adjusted fluidly with the monitored parameter of the drive assembly (drive element speed, in this instance). This can allow for a more adaptable motor control algorithm that can provide a surgeon with varying drive element speed while minimizing the risk of motor stall no matter what speed the surgeon, or a surgical robot, is actuating the drive element.

In accordance with the present disclosure, the control circuit 2004 can be configured to switch between a first drive configuration of the gear box to provide a first inertia value and a second drive configuration of the gear box to provide a second inertia value. The first drive configuration may include a slower speed but more torque while the second drive configuration may include an increased speed but less torque. The drive configurations may be switched between automatically by the control circuit 2004 or manually by a clinician. In accordance with the present disclosure, a solenoid may be provided to switch between different drive configurations. The first drive configuration provides a first amount of storable kinetic energy while the second drive configuration provides a second amount of storable kinetic energy which is greater than the first amount of storable kinetic energy. The drive configuration can be chosen by the control circuit 2004 depending on the minimum kinetic energy threshold of the current stage of the drive stroke. Additionally, the drive configuration can be chosen by the control circuit 2004 depending on stored kinetic energy of the drive assembly at a given time. For example, as the stored kinetic energy falls, the drive configuration may switch to the higher torque, lower speed configuration.

In accordance with the present disclosure, a target speed for the drive element may be selected based on the desired stored kinetic energy for the stage of the drive stroke. If motor stall risk is relatively low, a lower target speed may be selected. If motor stall risk is relatively high, a higher target speed may be selected to ensure a maximum amount of storable kinetic energy. Tissue thickness and/or clamping load can affect the velocity of the drive element and thus storage of kinetic energy in the drive assembly. Thicker tissue may increase the load on the drive element and decrease the speed of the drive element. This can reduce the stored kinetic energy in the drive assembly. Thinner tissue may decrease the load on the drive element and maintain a consistently higher speed of the drive element. This can increase the amount of stored kinetic energy in the drive assembly.

As discussed herein, motor adjustments can be made by the control circuit 2004 in an effort to overcome a potential stall condition. The motor adjustments can include any suitable adjustment such as those described herein. In accordance with the present disclosure, motor input voltage and/or current can be adjusted. A drive configuration of a gear box can be adjusted to change the amount of available kinetic energy to overcome the potential stall condition. Once a motor stalls, it may be significantly more difficult for a motor to restart a drive stroke. Motor stall may require reversing the drive element before re-advancing the drive element through the rest of the drive stroke. Such a motion may introduce a degree of unpredictability in forming the rest of the staples and/or cutting tissue through the rest of the drive stroke. The increased load on the drive element for restarting a drive element after a motor stall can present unnecessary stress and strain on drive assembly components. Additionally, motor stall may introduce voltage sag in a battery source for the motor and affect the integrity of the battery for future use. Motor stall may damage the motor, mechanical drive train components, gear box gears, etc. Providing a motor-adjustment when detecting a potential stall condition can provide a kinetic buffer to reduce the likelihood of motor stall.

Reducing motor stall of a surgical stapling instrument can increase longevity of the instrument and its components (battery, motor, etc.), increase the reliability of a surgical stapling and cutting drive stroke (ensure proper staple formation and clean tissue-cutting), increase confidence in surgeon to perform each drive stroke, reduce time of the drive stroke and, thus, the surgical stapling operation.

Figure 18:
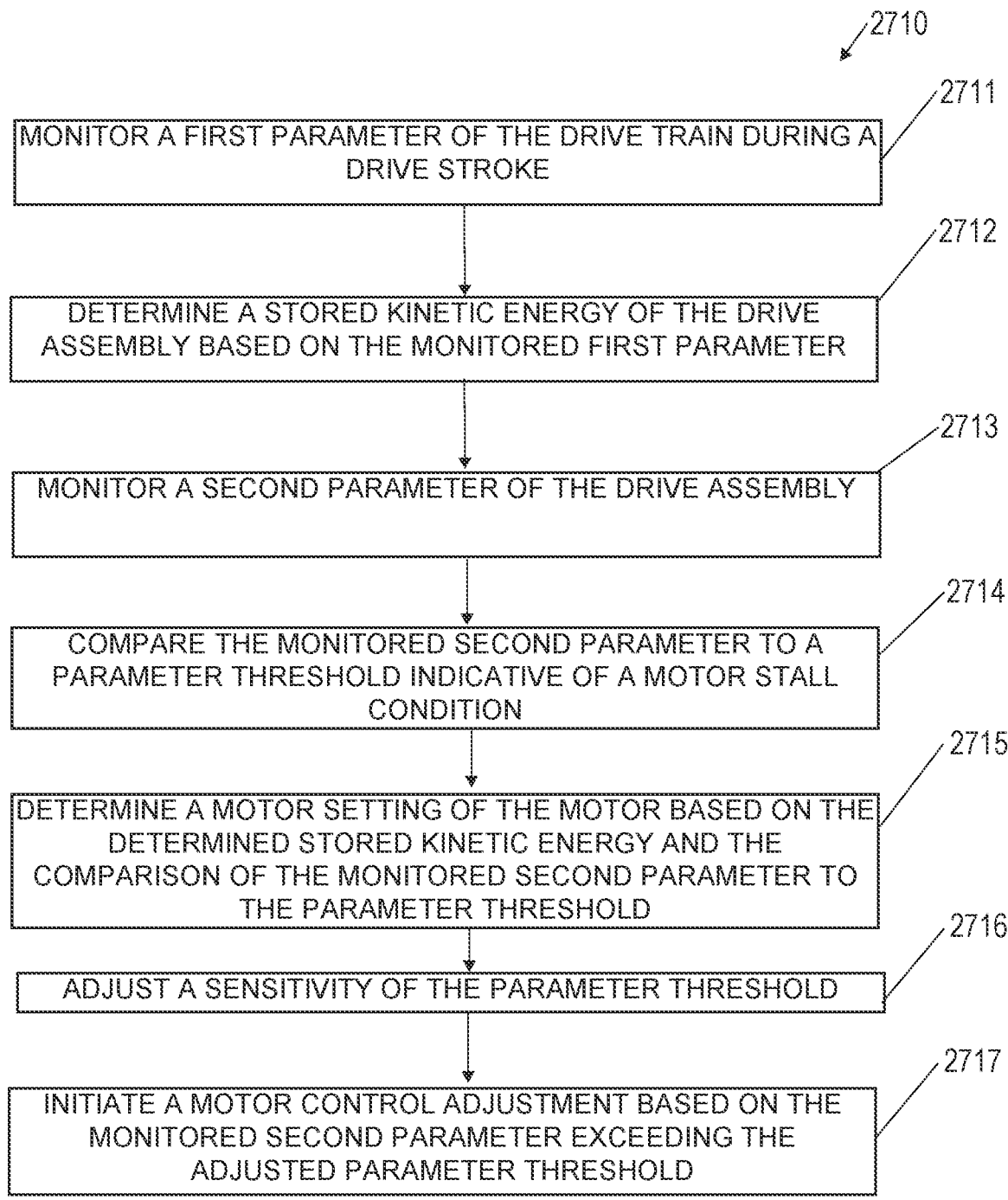
FIG. 18 is a logic flow diagram configured to be executed by a control circuit, wherein the control circuit is configured to adjust a sensitivity of a parameter threshold indicative of a motor stall condition, in accordance with the present disclosure.

FIG. 18 is a logic flow chart depicting a process 2710 executable by a control circuit, such as the control circuit 2004 illustrated in FIG. 1, for example, for controlling the motor of a drive assembly of a surgical stapling system such as those disclosed herein. The control circuit 2004 is coupled to a motor assembly 2009 including a motor, a drive element (e.g., firing beam), and a drive train connecting the motor and drive element. The drive train is actuatable by the motor to move the drive element through a drive stroke. In accordance with the present disclosure, the drive stroke may comprise a lockout stage, an initial clamping stage, a tissue cutting and stapling stage, and an ending stage. The control circuit 2004 is usable with the drive assembly, drive components, and surgical instrument components described herein.

The control circuit 2004 is configured to monitor 2711 a first parameter of the drive assembly during the drive stroke. As discussed herein, the first parameter may include any suitable parameter or combination of parameters indicative of the stored kinetic energy of the drive assembly. Such a parameter can include, for example, an output speed of the motor. The control circuit 2004 is further configured to determine 2712 a stored kinetic energy of the drive assembly based on the monitored 2711 first parameter. As discussed herein, determining the stored kinetic energy of the drive assembly can be achieved by utilizing known values of the drive assembly such as, for example, inertial mass, gear set moment arms, etc., and utilizing the monitored first parameter such as, for example, output speed of the drive train. This information can be used to calculate the total stored kinetic energy at any given moment during the drive stroke. In accordance with the present disclosure, the stored kinetic energy of the drive assembly may vary over time owing to external factors such as tissue load, for example, and/or owing to controllable inputs such as, for example, motor voltage/speed.

The control circuit 2004 is further configured to monitor 2713 a second parameter of the drive assembly during the drive stroke. In accordance with the present disclosure, the first parameter and the second parameter may be different. The second parameter may comprise tissue-induced load on the drive element, for example. Additionally, the monitored second parameter may be utilized to help detect a potential, or imminent, stall condition during the drive stroke. In the example of tissue-induced load on the drive element, a certain tissue load magnitude can indicate a potential stall condition. A threshold rate of increase of tissue load on the drive element can indicate a potential stall condition. As discussed herein, a combination of parameters can be utilized to help detect and/or alert of a potential stall condition. For example, in addition to tissue load on the drive element, drive element output speed can also be monitored and when the drive element speed and the tissue-induced load on the drive element meet a predetermined criteria, a potential stall condition can be indicated.

The control circuit is further configured to compare 2714 the monitored second parameter to a parameter threshold indicative of a motor stall condition. Such a parameter threshold may indicate a need for motor adjustment to prevent the motor from stalling. As discussed herein, the parameter threshold can include an acceptable percentage change in the monitored second parameter or the surpassing of a straight threshold value of the monitored second parameter, for example, before a motor adjustment is suggested or even necessary to prevent motor stall.

The control circuit 2004 is further configured to determine 2715 a motor setting of the motor based on the determined stored kinetic energy and the comparison of the monitored second parameter to the parameter threshold. The motor setting can include any suitable motor setting. In accordance with the present disclosure, the control circuit 2004 may determine to keep the motor setting the same. Additionally, the control circuit 2004 may determine that the stored kinetic energy of the drive assembly is adequate to overcome the potential stall condition with the current motor setting. The control circuit 2004 may adjust the motor setting such as, for example, increasing the speed of the motor, to increase kinetic energy in an effort to overcome the potential stall condition.

The control circuit 2004 is further configured to adjust 2716 a sensitivity of the parameter threshold indicative of a motor stall condition. In accordance with the present disclosure, the sensitivity of the parameter threshold may be a tolerance of acceptable variation of the monitored second parameter relative to the parameter threshold that indicates a motor stall condition. For example, as the stored kinetic energy increases, the control circuit 2004 can set a more tolerant parameter threshold to allow for more load on the firing beam before making a motor adjustment, for example, with the understanding that the drive assembly contains enough stored kinetic energy to overcome the increased load, or increased parameter threshold. On the other hand, the control circuit 2004 can set a more stringent parameter threshold, or tighten the tolerance of the parameter threshold, so that as the stored kinetic energy decreases, for example, even a slight load on the firing beam may indicate a motor stall condition.

In accordance with the present disclosure, the sensitivity of the parameter threshold may be based on the determined 2712 stored kinetic energy of the drive assembly. As discussed herein, the sensitivity of the parameter threshold can be represented by the magnitude of change of the monitored second parameter which would require a motor adjustment to prevent motor stall. In other words, the tolerance of change of the monitored second parameter before a motor adjustment is initiated can be decreased as the stored kinetic energy decreases. The tolerance of change of the monitored second parameter before a motor adjustment is initiated can be increased as the stored kinetic energy increases. As discussed herein, more stored kinetic energy can allow for a greater variance of the monitored second parameter before initiating a motor adjustment to prevent motor stall because the drive assembly has more kinetic energy to serve as a kinetic buffer through an imminent stall condition.

In accordance with the present disclosure, the tolerance level of variance of the monitored second parameter before initiating a motor adjustment may be tightened as the stored kinetic energy decreases. Similarly, the tolerance level of variance of the monitored second parameter before initiating a motor adjustment can be widened as the stored kinetic energy increases. The tolerance level, or sensitivity, may be adjusted from a 10% acceptable increase threshold of tissue-induced load on the drive element for a first kinetic energy to a 5% acceptable increase threshold of tissue-induced load on the drive element for a second kinetic energy where the second kinetic energy is lower than the first kinetic energy.

In accordance with the present disclosure, the motor control adjustment can be initiated 2717 based on the monitored second parameter exceeding the adjusted parameter threshold. Any suitable motor control adjustment can be initiated such as those disclosed herein. For example, the speed of the motor may be increased to a maximum level in an effort to increase the kinetic energy and, thus, stored kinetic energy to provide a kinetic buffer through the imminent stall condition.

While stall conditions are generally indicated as the events to be prevented, other drive assembly-related events can be monitored and used as the triggering event for sensitivity adjustments, motor control adjustments, and/or stored kinetic energy adjustments. For example, battery integrity of a battery powering a motor can be monitored and kinetic buffers can be utilized to help reduce the load on the battery over time. In accordance with the present disclosure, motor heat may effect motor efficiency over time and can be used to trigger kinetic buffers so as to help reduce motor heat during the life of the motor and/or during a single drive stroke, for example, of the motor.

While surgical stapling drive strokes are generally described in connection with the drive assemblies, control circuits, and processes disclosed herein, it can be appreciated that the drive assemblies, control circuits, and processes can be employed with a separate closure motor and/or closure drive assembly.

Figure 19:
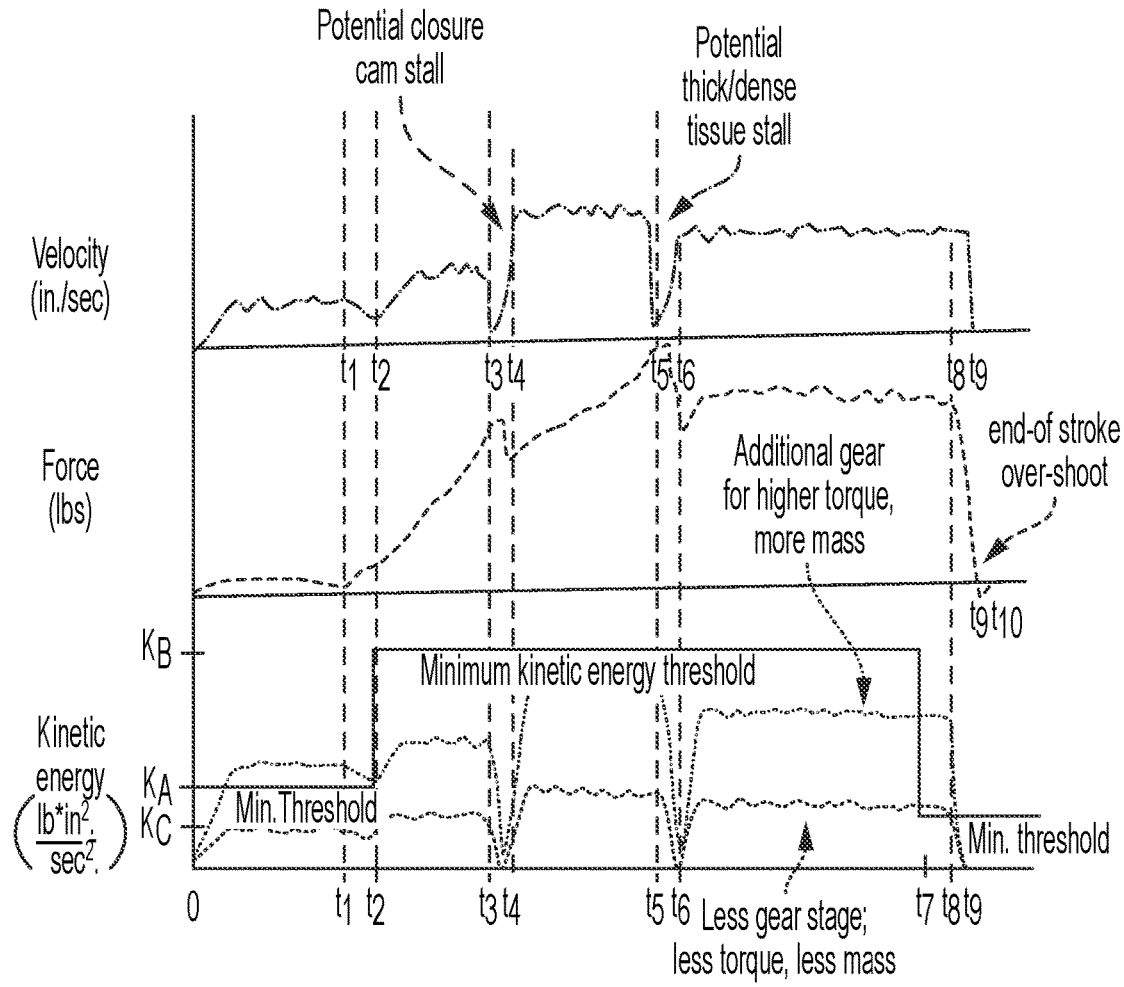
FIG. 19 is a graph of an example drive stroke of a surgical instrument employing the logic flow diagram of FIG. 18, in accordance with the present disclosure.

FIG. 19 is graph 2720 illustrating the velocity, force (load), and kinetic energy of an example drive stroke of a surgical stapling instrument such as those disclosed herein. As can be seen in FIG. 19, potential stall conditions are encountered at t3 and t5. These stall conditions can be overcome utilizing the control circuits, drive assemblies and components, and/or control circuit processes disclosed herein. The kinetic energy of multiple gear sets within a gear box of the drive assembly is also depicted in the graph 2720. As can be seen in the graph 2720, the kinetic energy of each gear set is different during different stages of the drive stroke. A minimum kinetic energy threshold is utilized and is different for various stages of the drive stroke. A control circuit (e.g., control circuit 2004) is configured to monitor the kinetic energies of each gear set relative to the minimum kinetic energy and, while also monitoring for potential stall conditions, ensure that a proper amount of kinetic energy in the drive assembly is maintained during the drive stroke provide a sufficient kinetic buffer through the stall events.

Still referring to FIG. 19, the minimum kinetic energy threshold may be set at its highest during the part of the drive stroke where the jaws are clamped, tissue is cut, and tissue is stapled. Maximum kinetic energy storage may be preferred during this period. As discussed herein, one or more other parameters are configured to be monitored during the drive stroke. These parameters are compared with a parameter threshold and, when the parameter threshold is met, an adjustment is made to the motor (maximize motor output speed, for example) to maintain kinetic energy through a potential stall event. The control circuit 2004 is further configured to adjust a sensitivity of the motor-adjustment trigger thresholds in real time during the drive stroke. In accordance with the present disclosure, the sensitivity of the parameter thresholds may be much greater (a more stringent tolerance) at lower speeds during the drive stroke whereas the sensitivity of the parameter thresholds may be much lower (a less stringent tolerance) at higher speeds during the drive stroke.

The minimum kinetic energy threshold is also configured to be adjusted based on a zone within which the drive element is positioned during the drive stroke. As discussed herein, maintaining a particular kinetic energy through particular sections of the drive stroke can increase reliability and predictability of the drive stroke reducing the possibility of motor stall, for example. A system which simply increases the motor speed to a maximum for example ahead of a potential stall condition may be undesirable. In accordance with the present disclosure, maximizing motor speed during the staple firing and tissue-cutting part of the drive stroke may be okay while maximizing motor speed during the tissue clamping part of the drive stroke may clamp tissue too quickly or apply too much pressure to tissue compared to the desired levels of the user. Thus fine tuning the kinetic buffer can ensure proper amounts of speed and force are applied during specific parts of the drive stroke without overcompensating, for example, ahead of a potential stall condition.

In accordance with the present disclosure, a potential stall condition near, at, or after the staple firing and tissue-cutting part of the stroke may not be as important to buffer as a potential stall condition during other parts of the stroke. The control circuit 2004 can be configured to adjust the motor control program so as to not ram the drive element into the end of the end effector in the event of detecting a potential stall condition.

Various aspects of the subject matter described herein are set out in the following examples.

Example 1—A surgical stapling system (2002) comprising a motor (2009), a drive assembly (2011) comprising a drive train (2200) coupled to the motor to actuate a function of a surgical end effector, wherein the drive train is actuatable by the motor through a drive stroke, and a control circuit (2004) coupled to the drive assembly, wherein the control circuit is configured to monitor (2711) a first parameter of the drive assembly during the drive stroke, determine (2712) a stored kinetic energy of the drive assembly based on the first parameter, monitor (2713) a second parameter of the drive assembly during the drive stroke, wherein the first parameter and the second parameter are different, compare (2714) the monitored second parameter to a parameter threshold indicative of a motor stall condition, and determine (2715) a motor setting of the motor based on the determined stored kinetic energy and the comparison of the monitored second parameter to the parameter threshold.

Example 2—The surgical stapling system of Example 1, wherein the motor setting comprises a sensitivity of the parameter threshold, and wherein the control circuit is further configured to adjust the sensitivity of the parameter threshold by decreasing the sensitivity of the parameter threshold based on an increase in the determined stored kinetic energy.

Example 3—The surgical stapling system of Examples 1 or 2, wherein the motor setting comprises a sensitivity of the parameter threshold, and wherein the control circuit is further configured to adjust the sensitivity of the parameter threshold by increasing the sensitivity of the parameter threshold based on a decrease in the determined stored kinetic energy.

Example 4—The surgical stapling system of Examples 2 or 3, wherein the control circuit is further configured to initiate a motor control adjustment based on the monitored second parameter exceeding the adjusted parameter threshold.

Example 5—The surgical stapling system of Example 4, wherein the motor control adjustment comprises increasing a kinetic energy of the drive assembly.

Example 6—The surgical stapling system of Examples 1, 2, 3, 4, or 5, wherein the control circuit is further configured to maintain a minimum kinetic energy threshold of the drive assembly during the drive stroke, and wherein the minimum kinetic energy threshold is adjusted based on a zone within which a driver drivable by the drive train is positioned during the drive stroke.

Example 7—The surgical stapling system of Examples 1, 2, 3, 4, 5, or 6, wherein the first parameter comprises a velocity of a driver drivable by the drive train.

Example 8—The surgical stapling system of Example 7, wherein the second parameter comprises a load on the driver.

Example 9—The surgical stapling system of Examples 1, 2, 3, 4, 5, 6, 7, or 8, wherein the second parameter comprises a velocity of a driver drivable by the drive train.

Example 10—The surgical stapling system of Examples 1, 2, 3, 4, 5, 6, 7, 8, or 9, wherein the first parameter comprises a rotational velocity of a gear stage within the drive train.

Example 11—The surgical stapling system of Examples 1, 2, 3, 4, 5, 6, 7, 8, 9, or 10, wherein the control circuit is further configured to switch from a first drive configuration of the drive assembly including a first inertia value to a second drive configuration of the drive assembly including a second inertia value, wherein the second inertia value is different than the first inertia value.

Example 12—The surgical stapling system of Example 11, wherein the control circuit is configured to switch from the first drive configuration to the second drive configuration based on the second parameter exceeding a predetermined parameter stall threshold.

Example 13—The surgical stapling system of Example 12, wherein the predetermined parameter stall threshold is greater than the parameter threshold.

Example 14—The surgical stapling system of Examples 1, 2, 3, 4, 5, 6, 7, 8, 9, 10, 11, 12, or 13, wherein the drive train comprises a variable flywheel for adjusting the amount of storable kinetic energy of the drive assembly during the drive stroke.

Example 15—A surgical stapling system comprising a motor, a drive assembly comprising a drive train coupled to the motor to actuate a function of a surgical end effector, wherein the drive train is actuatable by the motor through a drive stroke, and a control circuit coupled to the drive assembly. The control circuit is configured to monitor a first parameter of the drive assembly during the drive stroke, determine a stored kinetic energy of the drive assembly based on the first parameter, monitor a second parameter of the drive assembly during the drive stroke, wherein the first parameter and the second parameter are different, compare the monitored second parameter to a parameter threshold indicative of a motor stall condition, and determine a motor setting of the motor based on the determined stored kinetic energy and the comparison of the monitored second parameter to the parameter threshold.

Example 16—The surgical stapling system of Example 15, wherein the motor setting comprises a sensitivity of the parameter threshold, and wherein the control circuit is further configured to adjust the sensitivity of the parameter threshold by decreasing the sensitivity of the parameter threshold based on an increase in the determined stored kinetic energy.

Example 17—The surgical stapling system of Examples 15 or 16, wherein the motor setting comprises a sensitivity of the parameter threshold, and wherein the control circuit is further configured to adjust the sensitivity of the parameter threshold by increasing the sensitivity of the parameter threshold based on a decrease in the determined stored kinetic energy.

Example 18—The surgical stapling system of Examples 15, 16, or 17, wherein the control circuit is further configured to initiate a motor control adjustment based on the monitored second parameter exceeding the adjusted parameter threshold.

Example 19—The surgical stapling system of Examples 15, 16, 17, or 18, wherein the motor control adjustment comprises increasing a kinetic energy of the drive assembly.

Example 20—The surgical stapling system of Examples 15, 16, 17, 18, or 19, wherein the control circuit is further configured to maintain a minimum kinetic energy threshold of the drive assembly during the drive stroke, and wherein the minimum kinetic energy threshold is adjusted based on a zone within which a driver drivable by the drive train is positioned during the drive stroke.

Example 21—The surgical stapling system of Examples 15, 16, 17, 18, 19, or 20, wherein the first parameter comprises a velocity of a driver drivable by the drive train.

Example 22—The surgical stapling system of Examples 15, 16, 17, 18, 19, 20, or 21, wherein the second parameter comprises a load on the driver.

Example 23—The surgical stapling system of Examples 15, 16, 17, 18, 19, 20, 21, or 22, wherein the second parameter comprises a velocity of a driver drivable by the drive train.

Example 24—The surgical stapling system of Examples 15, 16, 17, 18, 19, 20, 21, 22, or 23, wherein the first parameter comprises a rotational velocity of a gear stage within the drive train.

Example 25—The surgical stapling system of Examples 15, 16, 17, 18, 19, 20, 21, 22, 23, or 24, wherein the control circuit is further configured to switch from a first drive configuration of the drive assembly including a first inertia value to a second drive configuration of the drive assembly including a second inertia value, wherein the second inertia value is different than the first inertia value.

Example 26—The surgical stapling system of Examples 15, 16, 17, 18, 19, 20, 21, 22, 23, 24, or 25, wherein the control circuit is configured to switch from the first drive configuration to the second drive configuration based on the second parameter exceeding a predetermined parameter stall threshold.

Example 27—The surgical stapling system of Examples 15, 16, 17, 18, 19, 20, 21, 22, 23, 24, 25, or 26, wherein the predetermined parameter stall threshold is greater than the parameter threshold.

Example 28—The surgical stapling system of Examples 15, 16, 17, 18, 19, 20, 21, 22, 23, 24, 25, 26, or 27, wherein the drive train comprises a variable flywheel for adjusting the amount of storable kinetic energy of the drive assembly during the drive stroke.

Example 29 A surgical stapling system comprising a motor, a drive assembly comprising a drive train coupled to the motor to actuate a firing driver of a surgical end effector, wherein the drive train is actuatable by the motor through a drive stroke to move the firing driver through a firing stroke, and a control circuit coupled to the drive assembly. The control circuit is configured to monitor a first parameter of the drive assembly during the drive stroke, determine a stored kinetic energy of the drive assembly based on the first parameter, monitor a second parameter of the firing driver during the drive stroke, wherein the first parameter and the second parameter are different, compare the monitored second parameter to a parameter threshold indicative of a motor stall condition, and determine a motor setting of the motor based on the determined stored kinetic energy and the comparison of the monitored second parameter to the parameter threshold.

Example 30—The surgical stapling system of Example 29, wherein the motor setting comprises a sensitivity of the parameter threshold, and wherein the control circuit is further configured to adjust the sensitivity of the parameter threshold by increasing the sensitivity of the parameter threshold based on a decrease in the determined stored kinetic energy.

Example 31—The surgical stapling system of Examples 29 or 30, wherein the control circuit is further configured to initiate a motor control adjustment based on the monitored second parameter exceeding the adjusted parameter threshold.

Example 32—The surgical stapling system of Examples 29, 30, or 31, wherein the motor control adjustment comprises increasing a kinetic energy of the drive assembly.

Example 33—A surgical stapling system comprising a motor, a sensor, a drive assembly comprising a drive train coupled to the motor to actuate a firing driver of a surgical end effector, wherein the drive train is actuatable by the motor through a drive stroke to move the firing driver through a firing stroke, and a control circuit coupled to the drive assembly. The control circuit is configured to monitor a first parameter of the drive assembly during the drive stroke, determine a stored kinetic energy of the drive assembly based on the first parameter, monitor a second parameter of the drive assembly with the sensor during the drive stroke, wherein the first parameter and the second parameter are different, compare the monitored second parameter to a parameter threshold indicative of a motor stall condition, and switch, upon determining that the monitored second parameter exceeds a predetermined parameter stall threshold, from a first drive configuration of the drive assembly comprising a first inertia to a second drive configuration of the drive assembly comprising a second inertia, wherein the second inertia is different than the first inertia.

Example 34—The surgical stapling system of Example 33, wherein the drive train comprises a manually adjustable flywheel for adjusting the amount of storable kinetic energy of the drive assembly during the drive stroke.

Many of the surgical instrument systems described herein are motivated by an electric motor; however, the surgical instrument systems described herein can be motivated in any suitable manner. In accordance with the present disclosure, the surgical instrument systems described herein can be motivated by a manually-operated trigger, for example. Additionally, in accordance with the present disclosure, the motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one ore more other embodiments without limitation. Also, where materials are disclosed for certain components, other materials may be used. According to various embodiments, a single component may be replaced by multiple components, and multiple components may be replaced by a single component, to perform a given function or functions. The foregoing description and following claims are intended to cover all such modification and variations.

While several configurations have been described, additional modifications are within the scope of the present disclosure, which is intended to cover any variations, uses, or adaptations of the disclosed configurations using its general principles.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. The instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" or "control system" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in one aspect. Thus, appearances of the phrases "in one aspect," "in an aspect," "in an exemplification," and "in one exemplification" in various places throughout the specification are not necessarily all referring to the same aspect. The particular features, structures or characteristics may be combined in any suitable manner in various aspects.

It is worthy to note that any reference numbers included in the appended claims are used to reference exemplary embodiments/elements described in the present disclosure. Accordingly, any such reference numbers are not meant to limit the scope of the subject matter recited in the appended claims.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

The invention claimed is:

1. A surgical stapling system, comprising:
   a motor;

a drive assembly comprising a drive train coupled to the motor to actuate a function of a surgical end effector, wherein the drive train is actuatable by the motor through a drive stroke; and a control circuit coupled to the drive assembly, wherein the control circuit is configured to:
monitor a first parameter of the drive assembly during the drive stroke;
determine a stored kinetic energy of the drive assembly based on the first parameter;
monitor a second parameter of the drive assembly during the drive stroke, wherein the first parameter and the second parameter are different;
compare the monitored second parameter to a parameter threshold indicative of a motor stall condition;
determine a motor setting of the motor based on the determined stored kinetic energy and the comparison of the monitored second parameter to the parameter threshold.

2. The surgical stapling system of claim 1, wherein the motor setting comprises a sensitivity of the parameter threshold, and wherein the control circuit is further configured to adjust the sensitivity of the parameter threshold by decreasing the sensitivity of the parameter threshold based on an increase in the determined stored kinetic energy.

3. The surgical stapling system of claim 1, wherein the motor setting comprises a sensitivity of the parameter threshold, and wherein the control circuit is further configured to adjust the sensitivity of the parameter threshold by increasing the sensitivity of the parameter threshold based on a decrease in the determined stored kinetic energy.

4. The surgical stapling system of claim 3, wherein the control circuit is further configured to initiate a motor control adjustment based on the monitored second parameter exceeding the adjusted sensitivity of the parameter threshold.

5. The surgical stapling system of claim 4, wherein the motor control adjustment comprises increasing a kinetic energy of the drive assembly.

6. The surgical stapling system of claim 1, wherein the control circuit is further configured to maintain a minimum kinetic energy threshold of the drive assembly during the drive stroke, and wherein the minimum kinetic energy threshold is adjusted based on a zone within which a driver drivable by the drive train is positioned during the drive stroke.

7. The surgical stapling system of claim 1, wherein the first parameter comprises a velocity of a driver drivable by the drive train.

8. The surgical stapling system of claim 7, wherein the second parameter comprises a load on the driver.

9. The surgical stapling system of claim 1, wherein the second parameter comprises a velocity of a driver drivable by the drive train.

10. The surgical stapling system of claim 1, wherein the first parameter comprises a rotational velocity of a gear stage within the drive train.

11. The surgical stapling system of claim 1, wherein the control circuit is further configured to switch from a first drive configuration of the drive assembly including a first inertia value to a second drive configuration of the drive assembly including a second inertia value, wherein the second inertia value is different than the first inertia value.

12. The surgical stapling system of claim 11, wherein the control circuit is configured to switch from the first drive configuration to the second drive configuration based on the second parameter exceeding a predetermined parameter stall threshold.

13. The surgical stapling system of claim 12, wherein the predetermined parameter stall threshold is greater than the parameter threshold.

14. The surgical stapling system of claim 1, wherein the drive train comprises a variable flywheel for adjusting an amount of storable kinetic energy of the drive assembly during the drive stroke.

15. A surgical stapling system, comprising:
a motor;
a drive assembly comprising a drive train coupled to the motor to actuate a firing driver of a surgical end effector, wherein the drive train is actuatable by the motor through a drive stroke to move the firing driver through a firing stroke; and
a control circuit coupled to the drive assembly, wherein the control circuit is configured to:
monitor a first parameter of the drive assembly during the drive stroke;
determine a stored kinetic energy of the drive assembly based on the first parameter;
monitor a second parameter of the firing driver during the drive stroke, wherein the first parameter and the second parameter are different;
compare the monitored second parameter to a parameter threshold indicative of a motor stall condition;
determine a motor setting of the motor based on the determined stored kinetic energy and the comparison of the monitored second parameter to the parameter threshold.

16. The surgical stapling system of claim 15, wherein the motor setting comprises a sensitivity of the parameter threshold, and wherein the control circuit is further configured to adjust the sensitivity of the parameter threshold by increasing the sensitivity of the parameter threshold based on a decrease in the determined stored kinetic energy.

17. The surgical stapling system of claim 16, wherein the control circuit is further configured to initiate a motor control adjustment based on the monitored second parameter exceeding the adjusted sensitivity of the parameter threshold.

18. The surgical stapling system of claim 17, wherein the motor control adjustment comprises increasing a kinetic energy of the drive assembly.

19. A surgical stapling system, comprising:
a motor;
a sensor;
a drive assembly comprising a drive train coupled to the motor to actuate a firing driver of a surgical end effector, wherein the drive train is actuatable by the motor through a drive stroke to move the firing driver through a firing stroke; and
a control circuit coupled to the drive assembly, wherein the control circuit is configured to:
monitor a first parameter of the drive assembly during the drive stroke;
determine a stored kinetic energy of the drive assembly based on the first parameter;
monitor a second parameter of the drive assembly with the sensor during the drive stroke, wherein the first parameter and the second parameter are different;
compare the monitored second parameter to a parameter threshold indicative of a motor stall condition;
switch, upon determining that the monitored second parameter exceeds a predetermined parameter stall threshold, from a first drive configuration of the drive assembly comprising a first inertia to a second drive configuration of the drive assembly comprising a second inertia, wherein the second inertia is different than the first inertia.

20. The surgical stapling system of claim 19, wherein the drive train comprises a manually adjustable flywheel for adjusting an amount of storable kinetic energy of the drive assembly during the drive stroke.

* * * * *